United States Patent
Drost et al.

(10) Patent No.: US 10,028,459 B2
(45) Date of Patent: Jul. 24, 2018

(54) TOMATO PLANTS WITH IMPROVED DISEASE RESISTANCE

(71) Applicant: SEMINIS VEGETABLE SEEDS, INC., St. Louis, MO (US)

(72) Inventors: Derek R. Drost, Penn Valley, CA (US); Elaine Graham, Davis, CA (US); Albert Grit, Ermelo (NL); Jacobus Hoogstraten, Wageningen (NL); Stephanie Pedroni, St. Louis, MO (US)

(73) Assignee: Seminis Vegetable Seeds, Inc., Woodland, CA (US)

( * ) Notice: Subject to any disclaimer, the term of this patent is extended or adjusted under 35 U.S.C. 154(b) by 0 days.

(21) Appl. No.: 15/148,804

(22) Filed: May 6, 2016

(65) Prior Publication Data

US 2016/0355839 A1 Dec. 8, 2016

Related U.S. Application Data

(60) Provisional application No. 62/167,788, filed on May 28, 2015.

(51) Int. Cl.
*A01H 5/08* (2018.01)
*A01H 1/04* (2006.01)

(52) U.S. Cl.
CPC ............ *A01H 1/04* (2013.01); *A01H 5/08* (2013.01)

(58) Field of Classification Search
None
See application file for complete search history.

(56) References Cited

U.S. PATENT DOCUMENTS

| 2013/0055465 A1 | 2/2013 | Gabor et al. |
| 2015/0047067 A1 | 2/2015 | Vecchio et al. |
| 2015/0082477 A1 | 3/2015 | Gabor et al. |

FOREIGN PATENT DOCUMENTS

WO  WO 2014/045206 A1  3/2014

OTHER PUBLICATIONS

Foolad, Majid (International Journal of Plant Genomics (2007), pp. 1-52).*

International Search Report and Written Opinion for PCT Application No. PCT/US16/031586, dated Aug. 12, 2016.
Bai et al., "QTLs for Tomato Powdery Mildew Resistance (*Oidium lycopersici*) in *Lycopersicon parviflorum* G1.1601 Co-localize with Two Qualitative Powdery Mildew Resistance Genes," *Mol Plant Microbe Interact*; 16:169-176; 2003.
Chunwongse et al., "Chromosomal localization and molecular-marker tagging of the powdery mildew resistance gene (Lv) in tomato," *Theor Appl Genet*; 89:76-79; 1994.
Peng et al., "Optimized breeding strategies for multiple trait integration: II. Process efficiency in event pyramiding and trait fixation," *Mol Breed*; 33:105-115; 2014.
Ronen et al., "Regulation of carotenoid biosynthesis during tomato fruit development: expression of the gene for lycopene epsilon-cyclase is down-regulated during ripening and is elevated in the mutant Delta," *Plant J*; 17:341-351; 1999.
Communication Pursuant to Rule 114(2) EPC from the European Patent Office regarding European Application No. 16800485.1, dated May 7, 2018.
Extract from TGRC resources, description of accession LA3118, retrieved from the Internet at <http://tgrc.ucdavis.edu/Data/Acc/AccDetail.aspx?AccessionNum=LA3118>, dated 1991.
Chunwongse et al., "Chromosomal localization and molecular-marker tagging of the powdery mildew resistance gene (Lv) in tomato," *Theor. Appl. Genet.* 89:76-79, 1994.
Description from NAKT 2014 of Calioso variety, dated Feb. 12, 2014.
Stamova et al., "Lv—as a symbol of the gene controlling resistance to *Leveillula taurica*," *Research Reports*, TGC Report 40, p. 36, 1990.
Technical Sheet of Canek F1 variety, published in 2015 in Mexico.
Yordanov et al., "*Leveillula taurica* resistance in the tomato," *Research Notes*, TGC Report No. 25, p. 24, 1975.
Stamova et al., "Resistance to *Leveillula taurica* (Lev.) Am." *Research Reports*, TGC Report No. 37, p. 73, 1987.
UPOV registration in Mexico of Canek variety from HM Clause, Inc., dated Nov. 25, 2013.
UPOV registration in Turkey of Calioso 72 153 RZ variety from Rijk Zwaan Tarim Tlc. Ltd. Stl., dated May 31, 2012.

* cited by examiner

*Primary Examiner* — Medina A Ibrahim
(74) *Attorney, Agent, or Firm* — Dentons US LLP; Matthew Madsen, Esq.

(57) ABSTRACT

The present disclosure provides tomato plants exhibiting resistance to *Leveillula taurica* (Lt) and lacking traits associated with linkage drag such as an undesirable orange fruit exocarp color. Such plants may comprise novel introgressed genomic regions associated with disease resistance from *S. chilense*. In certain aspects, compositions, including novel polymorphic markers and methods for producing, breeding, identifying, and selecting plants or germplasm with a disease resistance phenotype are provided.

26 Claims, 6 Drawing Sheets

| Recombinant | NL0231620 | markers located in CrtI-E gene | | NL0235137 | NL0235199 | p_M_PMLT_Lv-Ia | | NL0244884 | LV | HueAngle_u |
| | | NSLYC009407170 | NSLYC009406370 | | | NL0235118 | NL0244887 | | | |
| | 15.5 | 17.25 | 17.28 | 18.6 | 23.4 | 24 | 26.8 | 33.5 | | |
| | 2,107,164 | 2,263,185 | 2,266,440 | 2,379,860 | 2,803,705 | 2,860,477 | 3,106,864 | 3,690,072 | | |
| R030 | AA | CC | AA | GG | GG | ** | ** | AA | R | 45.3360357 |
| R031 | AA | CC | AA | GG | GG | ** | ** | AA | R | 45.3273548 |
| R035 | AA | CC | AA | GG | GG | ** | ** | AA | R | 44.6267763 |
| R036 | AA | CC | AA | GG | AA | ** | ** | AA | R | 44.4807048 |
| R037 | AA | CC | AA | GG | GG | ** | ** | AA | R | 44.4200746 |
| R038 | AA | CC | AA | GG | GG | ** | ** | AA | R | 44.0079671 |

FIG. 4

| MRN | gen pos | phy pos | S | R1 | R2 | R3 | R4 | R5 | R6 | R7 | S1 | S2 | SO1 | SO2 |
|---|---|---|---|---|---|---|---|---|---|---|---|---|---|---|
| NSLYC009407170 | 23.65 | 2.29 Mb | CC | CC | CC | CC | CC | CC | CC | CC | CC | CC | TT | TT |
| NSLYC009406370 | 23.68 | 2.29 Mb | AA | AA | AA | AA | AA | AA | AA | AA | AA | AA | GG | GG |
| NL0235137 | 25.21 | 2.42 Mb | GG | GG | GG | GG | GG | GG | GG | GG | GG | GG | TT | TT |
| NSLYC009423970 | 29.8 | 2.82Mb | TT | AA | AA | TT | TT | TT | TT | TT | TT | TT | AA | AA |
| NL0235199 | 30.39 | 2.87Mb | AA | GG | GG | GG | GG | GG | AA | AA | AA | AA | GG | GG |
| NL0235118 | 31.1 | 2.92Mb | INS | DEL | DEL | DEL | DEL | DEL | DEL | INS | INS | INS | INS | DEL |
| NL0244887 | 34.69 | 3.20Mb | DEL | DEL | DEL | DEL | DEL | DEL | DEL | TT | TT | TT | DEL | TT |
| NL0244884 | 43.44 | 3.81Mb | AA | AA | AA | AA | AA | AA | AA | GG | GG | AA | AA | GG |
| | | Hue angle → | 45.23 | 44.01 | 44.42 | 45.33 | 44.63 | 45.34 | 44.48 | 47.68 | 45.38 | 48.07 | 53.93 | 55.64 |
| | | Line* → | S | R1 | R2 | R3 | R4 | R5 | R6 | R7 | S1 | S2 | SO1 | SO2 |

* Lines R1-R7 are resistant NILs, S1-S2 are susceptible, SO1-SO2 are susceptible and have the orange phenotype, S is FIR-16-2063/FDR-15-2031, and R is FIR-16-2138/FDR-15-2031.

CROSS-REFERENCE TO RELATED APPLICATIONS

This application claims the priority of U.S. Provisional Appl. Ser. No. 62/167,788, filed May 28, 2015, the entire disclosure of which is incorporated herein by reference.

FIELD OF THE INVENTION

The present invention relates to the field of agriculture and more specifically to methods and compositions for producing tomato plants exhibiting disease resistance and improved fruit quality.

INCORPORATION OF SEQUENCE LISTING

The sequence listing that is contained in the file named "SEMB020US_ST25," which is 34.5 kilobytes as measured in Microsoft Windows operating system and was created on May 6, 2016, is filed electronically herewith and incorporated herein by reference.

BACKGROUND OF THE INVENTION

Disease resistance is an important trait in agriculture, particularly for the production of food crops. Although disease resistance alleles have been identified in uncultivated tomato lines, efforts to introduce these alleles into cultivated lines are hindered by the introduction of deleterious traits together with the resistance alleles. The use of marker-assisted selection (MAS) in plant breeding methods has made it possible to select plants based on genetic markers linked to traits of interest. However, accurate markers for identifying or tracking desirable traits in plants are frequently unavailable even if a gene associated with the trait has been characterized. These difficulties are further complicated by factors such as polygenic or quantitative inheritance, and an often incomplete understanding of the genetic background underlying expression of a desired phenotype. Therefore, in the absence of accurate and validated markers for use in MAS, it may not be feasible to produce new plant lines exhibiting certain disease-resistant phenotypes.

SUMMARY OF THE INVENTION

In one aspect, the invention provides a tomato plant of a cultivated tomato plant variety comprising a recombinant introgression from *Solanum chilense* on chromosome 12, wherein said recombinant introgression comprises a first allele conferring improved resistance to *Leveillula taurica* (Lt) relative to a plant lacking said first allele, and wherein said recombinant introgression lacks a second allele from *Solanum chilense* genetically linked to said first allele, wherein the second allele would confer orange fruit exocarp if present in said recombinant introgression. In one embodiment, the recombinant introgression from *Solanum chilense* is located between approximately 2.42 Mbp and 3.19 Mbp on chromosome 12. In another embodiment, the recombinant introgression from *Solanum chilense* is located between approximately 2.93 Mbp and 2.99 Mbp on chromosome 12. In a further embodiment, the recombinant introgression from *Solanum chilense* is located between approximately: 2.55 Mbp and 3.09 Mbp; 2.42 Mbp and 3.03 Mbp; 2.42 Mbp and 3.18 Mbp; 2.85 Mbp and 3.09 Mbp; 2.85 Mbp and 3.19 Mbp; 2.91 Mbp and 2.99 Mbp; or 2.93 Mbp and 5.47 Mbp on chromosome 12. In a still further embodiment, the recombinant introgression from *Solanum chilense* is located between approximately: 2.85 Mbp and 3.09 Mbp; 2.85 Mbp and 3.19 Mbp; or 2.91 Mbp and 2.99 Mbp on chromosome 12. In another embodiment, the second allele is located in the genomic region encoding Crtl-E. In another embodiment, the plant comprises *S. chilense* donor DNA within a genomic segment flanked by NL0235137 and NL0244887. In another embodiment, the plant comprises a *Solanum chilense* allele at locus NL0235199 and locus NL0235118 and lacks a *Solanum chilense* allele at locus NL0235137 and locus NL0244887. In other embodiments, the invention provides a plant part of such a plant, or the plant part is a cell, a seed, a root, a stem, a leaf, a fruit, a flower, or pollen.

In another aspect, the invention provides a method for producing a tomato plant having improved resistance to *Leveillula taurica* (Lt) and lacking an orange fruit exocarp color, said method comprising: a) crossing the tomato plant of a cultivated tomato plant variety comprising a recombinant introgression from *Solanum chilense* on chromosome 12, wherein said recombinant introgression comprises a first allele conferring improved resistance to *Leveillula taurica* (Lt) relative to a plant lacking said first allele, and wherein said recombinant introgression lacks a second allele from *Solanum chilense* genetically linked to said first allele, wherein the second allele would confer orange fruit exocarp if present in said recombinant introgression with itself or with a second tomato plant of a different genotype to produce one or more progeny plants; and b) selecting a progeny plant comprising said recombinant introgression. In one embodiment, selecting said progeny plant comprises identifying a progeny plant that (1) comprises a *Solanum chilense* allele at a locus genetically linked to said first allele and/or lacks an allele present at the corresponding locus in the cultivated tomato plant variety, and (2) lacks a *Solanum chilense* allele at a locus genetically linked to said second allele that confers orange fruit exocarp color, and/or comprises an allele present at the corresponding locus from the cultivated tomato plant variety. In another embodiment, selecting said progeny plant comprises marker-assisted selection (MAS). In other embodiments, marker-assisted selection (MAS) comprises detecting at least one allele at a locus located between approximately 2.42 Mbp and 3.19 Mbp on chromosome 12, or marker-assisted selection (MAS) comprises detecting at least one allele at a locus located between approximately 2.93 Mbp and 2.99 Mbp on chromosome 12, or marker-assisted selection (MAS) comprises detecting at least one allele at a locus selected from the group consisting of NL0235199, NL0235118, NL0235137, and NL0244887. In another embodiment, the progeny plant is an F2-F6 progeny plant. In still further embodiments, producing the progeny plant comprises backcrossing, such as from 2-7 generations of backcrossing.

In another aspect, the invention provides a method for obtaining a tomato plant exhibiting improved resistance to *Leveillula taurica* (Lt) comprising: a) obtaining a tomato plant heterozygous for a first allele that confers resistance to *Leveillula taurica* (Lt) and that is genetically linked in the plant to a second allele from *Solanum chilense* that confers orange fruit exocarp color; (b) obtaining progeny of the plant; and (c) selecting at least a first progeny plant in which recombination has occurred such that the progeny comprises said first allele that confers resistance to *Leveillula taurica* (Lt) but not said second allele that confers orange fruit exocarp color; wherein selecting said first progeny plant comprises detecting at least one allele at a locus located between approximately 2.42 Mbp and 3.19 Mbp on chromosome 12. In one embodiment, selecting said first progeny comprises detecting at least one allele at a locus located between approximately 2.93 Mbp and 2.99 Mbp on chromosome 12. In another embodiment, selecting said first progeny comprises detecting at least one allele at a locus selected from the group consisting of NL0235199, NL0235118, NL0235137, and NL0244887. In a further embodiment, the progeny plant is an F2-F6 progeny plant. In still further embodiments, obtaining said progeny plant comprises backcrossing, such as from 2-7 generations of backcrossing. In another embodiment, the invention provides a plant produced by such a method. In another embodiment, the invention provides a part of such a plant, selected from the group consisting of a cell, a seed, a root, a stem, a leaf, a fruit, a flower, and pollen.

BRIEF DESCRIPTION OF THE DRAWINGS

FIG. 1: Shows the genotypes of recombinant inbred lines (RILs) at several genetic marker positions. The table is sorted by fruit color as shown in the column furthest to the right, which shows the least-squared mean (LSM) estimate of fruit color as measured by a*b* hue angle. Plant lines exhibiting a fruit color phenotype more similar to FIR-16-2138/FDR-15-2031 hybrids are shown at the top of the column, and plant lines exhibiting a phenotype more similar to FIR-16-2063/FDR-15-2031 hybrids at the bottom. Column "LV" indicates whether the plant line is resistant (R) or susceptible (S) to *Leveillula taurica* (Lt).

FIG. 2: Shows six recombinant inbred lines in which resistance to Lt was retained and unfavorable orange fruit exocarp color caused by the fruit color gene Delta was eliminated.

FIG. 4: Shows the genotypes of double recombinant progeny of FIR-16-2063/FIR-16-2138 at several genetic marker positions. DNA segments retained from the *S. chilense* introgression are shaded dark grey, recipient DNA segments are shaded lighter grey. Lines R1-R7 are resistant NILs, S1-S2 are susceptible, SO1-SO2 are susceptible and have the orange phenotype, S is FIR-16-2063/FDR-15-2031, and R is FIR-16-2138/FDR-15-2031.

DETAILED DESCRIPTION

Figure 3:
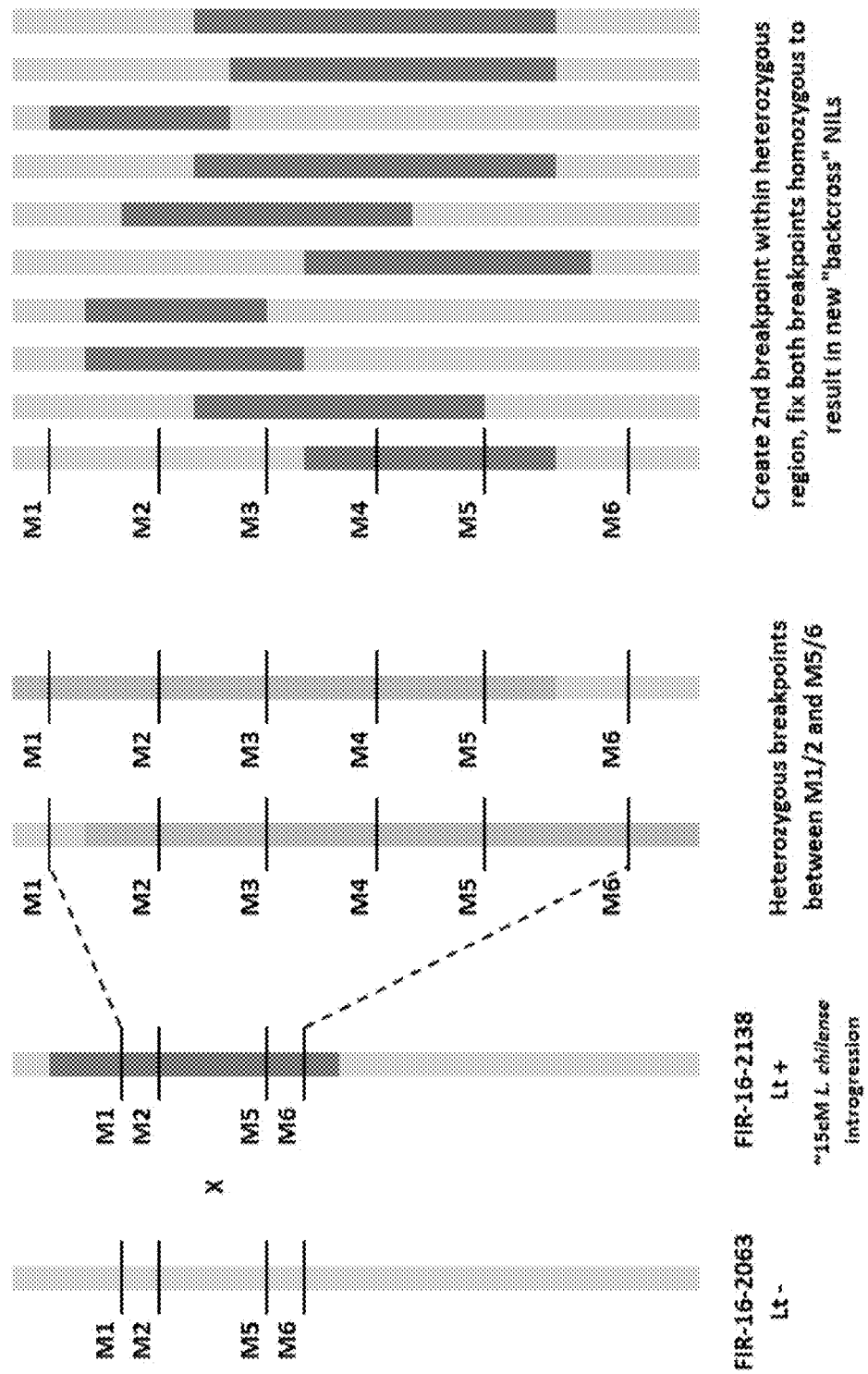
FIG. 3: Shows a molecular breeding strategy for producing novel near isogenic lines (NILs) for Lt resistance. Markers noted in the figure are hypothetical.

*Leveillula taurica* (Lt) is a plant fungal pathogen which causes powdery mildew in tomato, resulting in severe yield loss in tomato crops. Several wild tomato species are known to exhibit resistance to Lt, and intensive efforts have been made to introgress Lt resistance alleles from these species into cultivated tomato lines. However, these efforts have been hampered because introgressed Lt resistance alleles from wild species are accompanied by undesirable agronomic traits. Yield loss due to Lt in tomato plants therefore remains a significant problem.

For the first time, the invention provides novel introgressions of disease resistance alleles from *Solanum chilense* into cultivated tomato lines which result in plants exhibiting high levels of resistance to Lt without the deleterious traits typically associated with introgressions from wild species. The invention therefore represents a significant advance in the art. By further providing novel, accurate markers for tracking the introgressed alleles during plant breeding, the invention permits introgression of disease resistance into any desired tomato genotype.

Resistance to Lt has conventionally been obtained through introgressions of a locus on tomato chromosome 12 from *S. chilense*. However, such introgressions have to date exhibited unacceptable traits including orange fruit exocarp color. Efforts to reduce the incidence or severity of orange fruit color in plants comprising these introgressions have been unsuccessful in part due to a lack of existing markers and assays that accurately correlate genotype with resistance over a variety of tomato lines.

Despite the many obstacles to the successful introgression of resistance alleles from *S. chilense* into cultivated tomato lines, the present inventors were surprisingly able to produce novel introgressions from *S. chilense* which confer resistance to Lt without the deleterious traits previously associated with introgressions. The invention further identifies a novel QTL on tomato chromosome 12, as well as nucleic acid sequences and genetic markers associated with this novel QTL, which confer resistance to Lt without an undesirable orange fruit exocarp color. In some embodiments, the invention provides plants comprising donor *S. chilense* DNA at a first locus associated with improved resistance to Lt, and DNA from a recipient plant variety at a second locus associated with orange fruit exocarp color. In further embodiments, the invention provides plants comprising donor *S. chilense* DNA in a chromosomal region between 2.42 Mbp and 3.19 Mbp, or between 2.93 Mbp and 2.99 Mbp on chromosome 12.

The invention further provides novel trait-linked markers which can be used to produce plants comprising novel recombined introgressions in the region of chromosome 12 conferring Lt resistance, which result in plants exhibiting Lt resistance and also acceptable fruit exocarp color. In particular embodiments, the invention provides the markers shown in Table 1. Other embodiments of the invention provide novel markers NL0235199, NL0235118, NL0235137, and NL0244887, which have been shown to be genetically linked to Lt resistance in plants. Sequences for the markers in Table 1 are provided in Table 6.

In other embodiments, the invention provides methods of producing plants exhibiting Lt resistance and desirable fruit exocarp color by selecting or breeding plants having favorable alleles at markers within or genetically linked to the chromosomal segments disclosed herein. In some embodiments, the invention provides methods of selecting or breeding plants comprising detecting at least one allele at a locus selected from the group consisting of NL0235199, NL0235118, NL0235137, and NL0244887. In certain embodiments, the invention provides plants comprising *S. chilense* DNA at locus NL0235199 and locus NL0235118 and DNA originating from a recipient plant at locus NL0235137 and locus NL0244887. In other embodiments, the invention provides plants comprising *S. chilense* donor DNA within a genomic segment flanked by NL0235137 and NL0244887.

The novel markers and assays provided by the invention allow the accurate identification and tracking of the genomic regions provided herein during plant breeding, thereby enabling the production of plants exhibiting Lt resistance without undesirable fruit color. Because the introduction of Lt resistance alleles from genetically diverse tomato lines can result in suppressed recombination, marker-assisted selection (MAS) is essential for the successful introduction of Lt resistance alleles from *S. chilense* into cultivated lines without the accompanying undesirable fruit color alleles. The present invention enables MAS by providing improved and validated markers for detecting genotypes associated with disease resistance without the need to grow large populations of plants to maturity in order to observe this resistance. In certain embodiments, the invention provides plants comprising a recombinant introgression from *S. chilense* on chromosome 12 conferring improved Lt resistance relative to a plant lacking the recombinant introgression. The recombinant introgression further comprises a second allele genetically linked to said first allele that does not confer orange fruit exocarp color relative to a plant lacking the second allele. In some embodiments, the plants of the invention comprise *S. chilense* donor DNA between approximately 2.42 Mbp and 3.19 Mbp on chromosome 12. In further embodiments, the plants of the invention comprise *S. chilense* donor DNA between approximately 2.93 Mbp and 2.99 Mbp on chromosome 12

I. Genomic Regions, Alleles, and Polymorphisms Associated with Lt Resistance and Desirable Fruit Exocarp Color in Tomato Plants The invention provides novel introgressions of one or more alleles associated with disease tolerance and improved fruit exocarp color in tomato plants, together with polymorphic nucleic acids and linked markers for tracking the introgressions during plant breeding.

Lt infection causes a severe reduction in yield and quality in a tomato crop. Intensive efforts have therefore been made to identify effective sources of Lt resistance. However, previously known introgressions from wild species have not produced usable tomato crops due to insufficient levels of resistance or unacceptable associated deleterious traits. In particular, cultivated tomato lines carrying previously known introgressions of Lt resistance genes exhibit fruit with an undesirable orange exocarp color. Despite selective breeding in an effort to reduce the incidence of orange fruit exocarp color, these effects are still routinely observed in the field. Wild tomato types exhibiting Lt resistance, for example *S. chilense*, are known in the art and may be used in accordance with certain embodiments of the invention.

Using the improved genetic markers and assays of the invention, Applicants were able to successfully identify a novel Lt resistance region from *S. chilense* associated with fewer deleterious traits when introgressed into a cultivated line. In certain embodiments, the invention provides an *S. chilense* introgression conferring Lt resistance and without undesirable orange fruit color defined by genomic positions 2.44 Mbp and 3.18 Mbp on chromosome 12. In other embodiments, the invention provides a minimal efficacious introgression conferring Lt resistance and without undesirable orange fruit color defined by genomic positions 2.94 Mbp and 2.99 Mbp. The invention further provides plants comprising a *S. chilense* introgression located between approximately 2.94 Mbp and 3.04 Mbp, or between approximately 2.85 Mbp and 3.18 Mbp, or between approximately 2.92 Mbp and 2.99 Mbp on chromosome 12, which exhibit Lt resistance and acceptable fruit exocarp color.

In other embodiments, the invention provides plants comprising *S. chilense* donor DNA within a genomic segment flanked by markers NL0235137 and NL0244887. In further embodiments, the invention provides plants comprising donor *S. chilense* DNA at markers NL0235199 and NL0235118 and recipient DNA at markers NL0235137 and NL0244887.

The invention further identifies and provides genomic segments between approximately 2.55 Mbp and 3.08 Mbp; between approximately 2.44 Mbp and 3.03 Mbp; between approximately 2.44 Mbp and 3.15 Mbp; between approximately 2.94 Mbp and 3.04 Mbp; between approximately 2.85 Mbp and 3.18 Mbp; between approximately 2.92 Mbp and 2.99 Mbp; or between approximately 2.94 Mbp and 4.99 Mbp on chromosome 12 associated with Lt resistance, but not associated with orange fruit exocarp color when introgressed into cultivated tomato lines. In other embodiments, the invention provides plants exhibiting resistance to Lt, wherein such plants lack the lycopene epsilon cyclase (Crtl-E) allele conferring orange fruit exocarp color.

II. Introgression of Genomic Regions Associated with Disease Resistance

Marker-assisted introgression involves the transfer of a chromosomal region defined by one or more markers from a first genetic background to a second. Offspring of a cross that contain the introgressed genomic region can be identified by the combination of markers characteristic of the desired introgressed genomic region from a first genetic background and both linked and unlinked markers characteristic of the second genetic background.

The present invention provides novel accurate markers for identifying and tracking introgression of one or more of the genomic regions from *S. chilense* disclosed herein into cultivated lines. In certain embodiments, the invention provides the markers set forth in Table 1. Further embodiments of the invention provide novel markers NL0235199, NL0235118, NL0235137, and NL0244887, which have been shown to be genetically linked to Lt resistance in plants.

Markers within or linked to any of the genomic intervals of the present invention may be useful in a variety of breeding efforts that include introgression of genomic regions associated with disease resistance into a desired genetic background. For example, a marker within 40 cM, 20 cM, 15 cM, 10 cM, 5 cM, 2 cM, or 1 cM of a marker associated with disease resistance described herein can be used for marker-assisted introgression of genomic regions associated with a disease tolerant phenotype.

Tomato plants comprising one or more introgressed regions associated with a desired phenotype wherein at least 10%, 25%, 50%, 75%, 90%, or 99% of the remaining genomic sequences carry markers whose alleles match the recurrent parent genotype outside of the region targeted for Lt resistance introgression are also provided. Tomato plants comprising an introgressed region closely linked to, or adjacent to, the genomic regions and markers provided herein and associated with a disease resistance phenotype are also provided.

III. Development of Disease Resistant Tomato Varieties

For most breeding objectives, commercial breeders work within germplasm that is "cultivated," "cultivated type" or "elite." As used herein, "elite" or "cultivated" variety means any variety that has resulted from breeding and selection for superior agronomic performance. This germplasm is easier to breed because it generally performs well when evaluated for horticultural performance. A number of cultivated tomato (*S. lycopersicum* or *L. esculentum*) types have been developed which are agronomically elite and appropriate for commercial cultivation. However, the performance advantage a cultivated germplasm provides can be offset by a lack of allelic diversity. Breeders generally accept this tradeoff because progress is faster when working with cultivated material than when breeding with genetically diverse sources.

In contrast, when cultivated germplasm is crossed with non-cultivated germplasm, a breeder can gain access to novel alleles from the non-cultivated type. However, this approach presents significant difficulties due to fertility problems associated with crosses between diverse lines, and negative linkage drag from the non-cultivated parent. In tomato plants, non-cultivated types such as S. chilense can provide alleles associated with disease resistance. However, these non-cultivated types may have poor horticultural qualities such as vulnerability to certain deleterious traits or diseases.

The process of introgressing desirable resistance genes from non-cultivated lines into elite cultivated lines while avoiding problems with linkage drag or low heritability is a long and often arduous process. Success in deploying alleles derived from wild relatives therefore strongly depends on minimal or truncated introgressions that lack detrimental effects and reliable marker assays that replace phenotypic screens. Success is further defined by simplifying genetics for key attributes to allow focus on genetic gain for quantitative traits such as disease resistance. Moreover, the process of introgressing genomic regions from non-cultivated lines can be greatly facilitated by the availability of accurate markers for MAS.

One of skill in the art would therefore understand that the alleles, polymorphisms, and markers provided by the invention allow the tracking and introduction of any of the genomic regions identified herein into any genetic background. In addition, the genomic regions associated with disease resistance disclosed herein can be introgressed from one genotype to another and tracked using MAS. Thus, Applicants' discovery of accurate markers associated with disease resistance facilitates the development of tomato plants having beneficial phenotypes. For example, seed can be genotyped using the markers of the present invention in order to select for plants comprising desired genomic regions associated with disease resistance. Moreover, MAS allows identification of plants homozygous or heterozygous for a desired introgression.

Inter-species crosses can also result in suppressed recombination and plants with low fertility or fecundity. For example, suppressed recombination has been observed for the tomato nematode resistance gene Mi, the Mla and Mlg genes in barley, the Yr17 and Lr20 genes in wheat, the Run1 gene in grapevine, and the Rma gene in peanut. Meiotic recombination is essential for classical breeding because it enables the transfer of favorable alleles across genetic backgrounds, the removal of deleterious genomic fragments, and pyramiding traits that are genetically tightly linked. Therefore, in the absence of accurate markers, suppressed recombination forces breeders to enlarge segregating populations for progeny screens.

Phenotypic evaluation of large populations is time-consuming, resource-intensive and not reproducible in every environment. Marker-assisted selection offers a feasible alternative. Molecular assays designed to detect unique polymorphisms, such as SNPs, are versatile. However, they may fail to discriminate alleles within and among tomato species in a single assay. Structural rearrangements of chromosomes such as deletions impair hybridization and extension of synthetically labeled oligonucleotides. In the case of duplication events, multiple copies are amplified in a single reaction without distinction. The development and validation of accurate and highly predictive markers are therefore essential for successful MAS breeding programs.

IV. Molecular Assisted Breeding Techniques

Genetic markers that can be used in the practice of the present invention include, but are not limited to, restriction fragment length polymorphisms (RFLPs), amplified fragment length polymorphisms (AFLPs), simple sequence repeats (SSRs), simple sequence length polymorphisms (SSLPs), single nucleotide polymorphisms (SNPs), insertion/deletion polymorphisms (Indels), variable number tandem repeats (VNTRs), and random amplified polymorphic DNA (RAPD), isozymes, and other markers known to those skilled in the art. Marker discovery and development in crop plants provides the initial framework for applications to marker-assisted breeding activities (U.S. Patent Pub. Nos.: 2005/0204780, 2005/0216545, 2005/0218305, and 2006/00504538). The resulting "genetic map" is the representation of the relative position of characterized loci (polymorphic nucleic acid markers or any other locus for which alleles can be identified) to each other.

Polymorphisms comprising as little as a single nucleotide change can be assayed in a number of ways. For example, detection can be made by electrophoretic techniques including a single strand conformational polymorphism (Orita et al. (1989) Genomics, 8(2), 271-278), denaturing gradient gel electrophoresis (Myers (1985) EPO 0273085), or cleavage fragment length polymorphisms (Life Technologies, Inc., Gathersberg, Md.), but the widespread availability of DNA sequencing often makes it easier to simply sequence amplified products directly. Once the polymorphic sequence difference is known, rapid assays can be designed for progeny testing, typically involving some version of PCR amplification of specific alleles (PASA; Sommer, et al., Biotechniques 12(1), 82-87, 1992), or PCR amplification of multiple specific alleles (PAMSA; Dutton and Sommer, Biotechniques, 11(6), 700-7002, 1991).

Polymorphic markers serve as useful tools for assaying plants for determining the degree of identity of lines or varieties (U.S. Pat. No. 6,207,367). These markers form the basis for determining associations with phenotypes and can be used to drive genetic gain. In certain embodiments of methods of the invention, polymorphic nucleic acids can be used to detect in a tomato plant a genotype associated with disease resistance, identify a tomato plant with a genotype associated with disease resistance, and to select a tomato plant with a genotype associated with disease resistance. In certain embodiments of methods of the invention, polymorphic nucleic acids can be used to produce a tomato plant that comprises in its genome an introgressed locus associated with disease resistance. In certain embodiments of the invention, polymorphic nucleic acids can be used to breed progeny tomato plants comprising a locus associated with disease resistance.

Genetic markers may include "dominant" or "codominant" markers. "Codominant" markers reveal the presence of two or more alleles (two per diploid individual). "Dominant" markers reveal the presence of only a single allele. Markers are preferably inherited in codominant fashion so that the presence of both alleles at a diploid locus, or multiple alleles in triploid or tetraploid loci, are readily detectable, and they are free of environmental variation, i.e., their heritability is 1. A marker genotype typically comprises two marker alleles at each locus in a diploid organism. The marker allelic composition of each locus can be either homozygous or heterozygous. Homozygosity is a condition where both alleles at a locus are characterized by the same nucleotide sequence. Heterozygosity refers to different conditions of the allele at a locus.

Nucleic acid-based analyses for determining the presence or absence of the genetic polymorphism (i.e. for genotyping) can be used in breeding programs for identification, selection, introgression, and the like. A wide variety of genetic markers for the analysis of genetic polymorphisms are available and known to those of skill in the art. The analysis may be used to select for genes, portions of genes, QTL, alleles, or genomic regions that comprise or are linked to a genetic marker that is linked to or associated with disease resistance in tomato plants.

As used herein, nucleic acid analysis methods include, but are not limited to, PCR-based detection methods (for example, TaqMan assays), microarray methods, mass spectrometry-based methods and/or nucleic acid sequencing methods, including whole genome sequencing. In certain embodiments, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

One method of achieving such amplification employs the polymerase chain reaction (PCR) (Mullis et al. 1986 Cold Spring Harbor Symp. Quant. Biol. 51:263-273; European Patent 50,424; European Patent 84,796; European Patent 258,017; European Patent 237,362; European Patent 201,184; U.S. Pat. No. 4,683,202; U.S. Pat. No. 4,582,788; and U.S. Pat. No. 4,683,194), using primer pairs that are capable of hybridizing to the proximal sequences that define a polymorphism in its double-stranded form. Methods for typing DNA based on mass spectrometry can also be used. Such methods are disclosed in U.S. Pat. Nos. 6,613,509 and 6,503,710, and references found therein.

Polymorphisms in DNA sequences can be detected or typed by a variety of effective methods well known in the art including, but not limited to, those disclosed in U.S. Pat. Nos. 5,468,613, 5,217,863; 5,210,015; 5,876,930; 6,030,787; 6,004,744; 6,013,431; 5,595,890; 5,762,876; 5,945,283; 5,468,613; 6,090,558; 5,800,944; 5,616,464; 7,312,039; 7,238,476; 7,297,485; 7,282,355; 7,270,981 and 7,250,252 all of which are incorporated herein by reference in their entirety. However, the compositions and methods of the present invention can be used in conjunction with any polymorphism typing method to type polymorphisms in genomic DNA samples. These genomic DNA samples used include but are not limited to, genomic DNA isolated directly from a plant, cloned genomic DNA, or amplified genomic DNA.

For instance, polymorphisms in DNA sequences can be detected by hybridization to allele-specific oligonucleotide (ASO) probes as disclosed in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe.

Target nucleic acid sequence can also be detected by probe ligation methods, for example as disclosed in U.S. Pat. No. 5,800,944 where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz et al., *Genome Res.* 13:513-523, 2003); Cui et al., *Bioinformatics* 21:3852-3858, 2005). On any one microarray, it is expected there will be a plurality of target sequences, which may represent genes and/or noncoding regions wherein each target sequence is represented by a series of overlapping oligonucleotides, rather than by a single probe. This platform provides for high throughput screening of a plurality of polymorphisms. Typing of target sequences by microarray-based methods is disclosed in U.S. Pat. Nos. 6,799,122; 6,913,879; and 6,996,476.

Other methods for detecting SNPs and Indels include single base extension (SBE) methods. Examples of SBE methods include, but are not limited to, those disclosed in U.S. Pat. Nos. 6,004,744; 6,013,431; 5,595,890; 5,762,876; and 5,945,283.

In another method for detecting polymorphisms, SNPs and Indels can be detected by methods disclosed in U.S. Pat. Nos. 5,210,015; 5,876,930; and 6,030,787 in which an oligonucleotide probe having a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5'→3' exonuclease activity cleaves the probe and separates the reporter dye from the quencher dye resulting in increased fluorescence of the reporter.

In another embodiment, a locus or loci of interest can be directly sequenced using nucleic acid sequencing technologies. Methods for nucleic acid sequencing are known in the art and include technologies provided by 454 Life Sciences (Branford, Conn.), Agencourt Bioscience (Beverly, Mass.), Applied Biosystems (Foster City, Calif.), LI-COR Biosciences (Lincoln, Nebr.), NimbleGen Systems (Madison, Wis.), Illumina (San Diego, Calif.), and VisiGen Biotechnologies (Houston, Tex.). Such nucleic acid sequencing technologies comprise formats such as parallel bead arrays, sequencing by ligation, capillary electrophoresis, electronic microchips, "biochips," microarrays, parallel microchips, and single-molecule arrays.

Definitions

The following definitions are provided to better define the present invention and to guide those of ordinary skill in the art in the practice of the present invention. Unless otherwise noted, terms are to be understood according to conventional usage by those of ordinary skill in the relevant art.

As used herein, the term "plant" includes plant cells, plant protoplasts, plant cells of tissue culture from which tomato plants can be regenerated, plant calli, plant clumps and plant cells that are intact in plants or parts of plants such as pollen, flowers, seeds, leaves, stems, and the like.

As used herein, the term "population" means a genetically heterogeneous collection of plants that share a common parental derivation.

As used herein, the terms "variety" and "cultivar" mean a group of similar plants that by their genetic pedigrees and performance can be identified from other varieties within the same species.

As used herein, an "allele" refers to one of two or more alternative forms of a genomic sequence at a given locus on a chromosome.

A "Quantitative Trait Locus (QTL)" is a chromosomal location that encodes for at least a first allele that affects the expressivity of a phenotype.

As used herein, a "marker" means a detectable characteristic that can be used to discriminate between organisms. Examples of such characteristics include, but are not limited to, genetic markers, biochemical markers, metabolites, morphological characteristics, and agronomic characteristics.

As used herein, the term "phenotype" means the detectable characteristics of a cell or organism that can be influenced by gene expression.

As used herein, the term "genotype" means the specific allelic makeup of a plant.

As used herein, "elite" or "cultivated" variety means any variety that has resulted from breeding and selection for superior agronomic performance. An "elite plant" refers to a plant belonging to an elite variety. Numerous elite varieties are available and known to those of skill in the art of tomato breeding. An "elite population" is an assortment of elite individuals or varieties that can be used to represent the state of the art in terms of agronomically superior genotypes of a given crop species, such as tomato. Similarly, an "elite germplasm" or elite strain of germplasm is an agronomically superior germplasm.

As used herein, "recombinant introgression" refers to a genomic introgression from *Solanum chilense* conferring resistance to *Leveillula taurica* (Lt), wherein the introgression has undergone meiotic recombination to remove an allele genetically linked to the resistance trait that confers orange fruit exocarp. In one embodiment, plants of the invention lacking an orange fruit exocarp may have an LSM hue angle of approximately 45.2. In another embodiment, plants of the invention lacking an orange fruit exocarp may have an LSM hue angle of approximately 44.8969±0.34424. In still another embodiment, plants of the invention lacking an orange fruit exocarp may have an LSM hue angle of 46.963±0.39518. In another embodiment, such a plant may have an LSM hue angle of less than approximately 47.35, or less than approximately 48.1. In still another embodiment, such a plant may have an LSM hue angle of between 43.0 and 48.1.

As used herein, the term "introgressed," when used in reference to a genetic locus, refers to a genetic locus that has been introduced into a new genetic background, such as through backcrossing. Introgression of a genetic locus can be achieved through plant breeding methods and/or by molecular genetic methods. Such molecular genetic methods include, but are not limited to, various plant transformation techniques and/or methods that provide for homologous recombination, non-homologous recombination, site-specific recombination, and/or genomic modifications that provide for locus substitution or locus conversion.

As used herein, the term "linked" or "genetically linked," when used in the context of nucleic acid markers and/or genomic regions, means that the markers and/or genomic regions are located on the same linkage group or chromosome such that they tend to segregate together at meiosis.

A tomato plant of a cultivated tomato plant variety comprising a recombinant introgression from *Solanum chilense* on chromosome 12, wherein said recombinant introgression comprises a first allele conferring improved resistance to *Leveillula taurica* (Lt) relative to a plant lacking said first allele, and wherein said recombinant introgression lacks a second allele from *Solanum chilense* genetically linked to said first allele, wherein the second allele would confer orange fruit exocarp if present in said recombinant introgression As used herein, "resistance locus" means a locus associated with resistance or tolerance to disease. For instance, a resistance locus according to the present invention may, in one embodiment, control resistance or susceptibility for Lt.

As used herein, "resistance allele" means the nucleic acid sequence associated with resistance or tolerance to disease.

As used herein "resistance" or "improved resistance" in a plant to disease conditions is an indication that the plant is more able to reduce disease burden than a non-resistant or less resistant plant. Resistance is a relative term, indicating that a "resistant" plant is more able to reduce disease burden compared to a different (less resistant) plant (e.g., a different plant variety) grown in similar disease conditions. One of skill will appreciate that plant resistance to disease conditions varies widely, and can represent a spectrum of more-resistant or less-resistant phenotypes. However, by simple observation, one of skill can generally determine the relative resistance of different plants, plant varieties, or plant families under disease conditions, and furthermore, will also recognize the phenotypic gradations of "resistant."

One of skill will appreciate that plant resistance to disease conditions varies widely, and can represent a spectrum of more-resistant or less-resistant phenotypes. However, by simple observation, one of skill can generally determine the relative resistance or susceptibility of different plants, plant lines or plant families under disease conditions, and furthermore, will also recognize the phenotypic gradations of "resistant."

The term "about" is used to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When used in conjunction with the word "comprising" or other open language in the claims, the words "a" and "an" denote "one or more," unless specifically noted. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

EXAMPLES

Example 1

Identification of Recombinant Tomato Lines with Lt Resistance

A cross was made between the line FIR-16-2063 (Lt susceptible, fruit color gene Delta negative), a parent of the FIR-16-2063/FDR-15-2031 commercial hybrid, and FIR-16-2138 (Lt resistant, Delta positive). An introgression of Lt resistance alleles in FIR-16-2138 was derived from a large introgression from the wild tomato species *Solanum chilense*. The Lt susceptible parent FIR-16-2063 did not have the introgression.

The resulting converted hybrid tomato progeny exhibited resistance to Lt (FIR-16-2138/FDR-15-2031). However, these lines were found to exhibit an unacceptable orange fruit exocarp color, which is associated with the Lt introgression from *S. chilense*. The molecular markers shown in Table 1 were developed for identification of recombinants maintaining Lt resistance with reduced incidence of fruit possessing the undesirable orange color. Sequences related to these markers are provided in Table 6. Further studies determined that light fruit color co-segregates with resistance at a very high frequency due to a cis-linkage between the orange fruit color gene Delta and Lt resistance.

TABLE 1

Molecular markers on tomato chromosome 12 useful for tracking the Lt resistance QTL. Locus p_M_PMLT_Lv-WS is useful for tracking Lt resistance derived from breeding with the donor FIR-193-90760. Locus p_M_PMLT_Lv-La is useful for tracking Lt resistance derived from breeding with the line 'Laurica'.

| Marker | Physical Position | Genetic Position | Loci interrogated |
|---|---|---|---|
| NL0235137 | 2,379,680 | 18.5 | |
| NL0235199 | 2,803,705 | 23.4 | |
| NL0235118 | 2,860,477 | 24 | p_M_PMLT_Lv-La |
| NL0244887 | 3,106,864 | 26.8 | |

Example 2

Mapping Populations

The F1 population resulting from the cross of FIR-16-2063/FIR-16-2138 was selfed to obtain a segregating F2 population. The F2 population was then screened with molecular markers across the 20 cM region around the Lt QTL (Table 1). Twenty-three plants were observed to have a recombination between physical position 2,000,964 (genetic position 14.3) on the left edge, or physical position 3,983,080 (genetic position 36.2) on the right edge, and markers flanking the 20 cM Lt QTL target region. These plants were planted in a greenhouse to obtain F3 seeds.

In the F3 generation, multiple plants from the recombinant F2:3 families were screened to identify individuals with a fixed primary breakpoint and a secondary segregating recombination event on the opposite side of the target interval, resulting in the identification of plants with reduced introgression sizes relative to the original donor FIR-16-2138. Subsequent selfing generations were used to fix all breakpoints and increase seed.

Example 3

Evaluation of Lt Resistance and Orange Fruit Color in Mapping Populations

Testcross hybrids were produced using FDR-15-2031 as a tester for each recombinant inbred line. These testcross hybrids were evaluated for fruit color in a replicated field trial using a Konica-Minolta colorimeter, measuring fruit color at four points on the fruit (equator: two measurements; blossom end: one measurement; stem end: one measurement) and for resistance to Lt (pathology and field assays). Plants were grown in a randomized complete block design with 60" bed spacing in field trials. Four plants were grown per plot, spaced 15 inches between plants (4 ft between plots) for field trials. Prior to fruit color measurement, fruit maturity was normalized by tagging 15-18 fruits in each plot at the breaker stage, with 3-4 replicates tagged per day. Tagged fruits were harvested 7 days later, at which point they were promptly analyzed with the colorimeter.

Using 8 fruits per plot, the L*a*b* colorimeter values for fruit color were recorded. The L*a*b* score was used to calculate hue angle for the a*b* axis, following a standard conversion equation for this type of data, after it was determined that the variance in L* was <10% between all measurements across the entire dataset. Hue angle was calculated according to the formula: Hue Angle=1−(a tan 2(b*,a*))=a tan 2 (a*,b*). The output of the formula in Radians was then converted to degrees to arrive at the range from 0-90 for the value of Hue angle. The a*b* hue values were used to calculate per-data-point hue angle, which was then averaged across fruit then subjected to Analysis of Variance (ANOVA) for calculation of least-squared mean (LSM) estimate of hue angle on a per-entry (pedigree) basis. Plant lines exhibiting a fruit color phenotype similar to the FIR-16-2138/FDR-15-2031 hybrid (LSM hue angle of 55.64) were considered orange, and plant lines exhibiting a phenotype similar to the FIR-16-2063/FDR-15-2031 hybrid (LSM hue angle of 45.2) were considered red, or non-orange.

Pathology resistance or susceptibility classifications were formulated on the basis of scoring 10 seedlings in the greenhouse for pathology assay resistance rating, and five plants in the field for field resistance rating. Concordance in ratings between greenhouse and field assays was nearly 100%. The protocol used to assay pathology resistance rating is provided in Table 2.

TABLE 2

Protocol for Screening for pathogen resistance.

POWDERY MILDEW

| DISEASE | |
|---|---|
| Pathogen | *Leveillula taurica* |
| Isolate | California isolate |
| CULTURING | |
| Concentration | 1 × 10$^4$ conidia/ml |
| Quantification | Count the number of conidia per ml using a hemacytometer and dilute with RO water. |
| Host | Tomato: *Solanum lycopersicum* (formerly *Lycopersicon esculentum*) |
| Controls | High Resistance: Laurica. Susceptible: HP 375 (LTS), VFN8 |
| Planting Method | Double seed into 6-pak flats. Thin to 1 plant per cell when plants reach expanded cotyledon stage. Plant the controls in the middle of the flat. |
| INOCULATION | |
| Age/Stage of Plants at Inoculation | 3-4 true leaf stage, 20 days. |
| Inoculation Procedure | Using a spray bottle, uniformly spray the foliage of all plants. |
| EVALUATION | |
| Rating/Score Definition | This screen is read HR, IR, S, or 1, 5, 9. HR (1): No sporulation. IR (5): Very light sporulation. S (9): White sporulation on the whole surface of inoculated leaves. |

Figure 1:
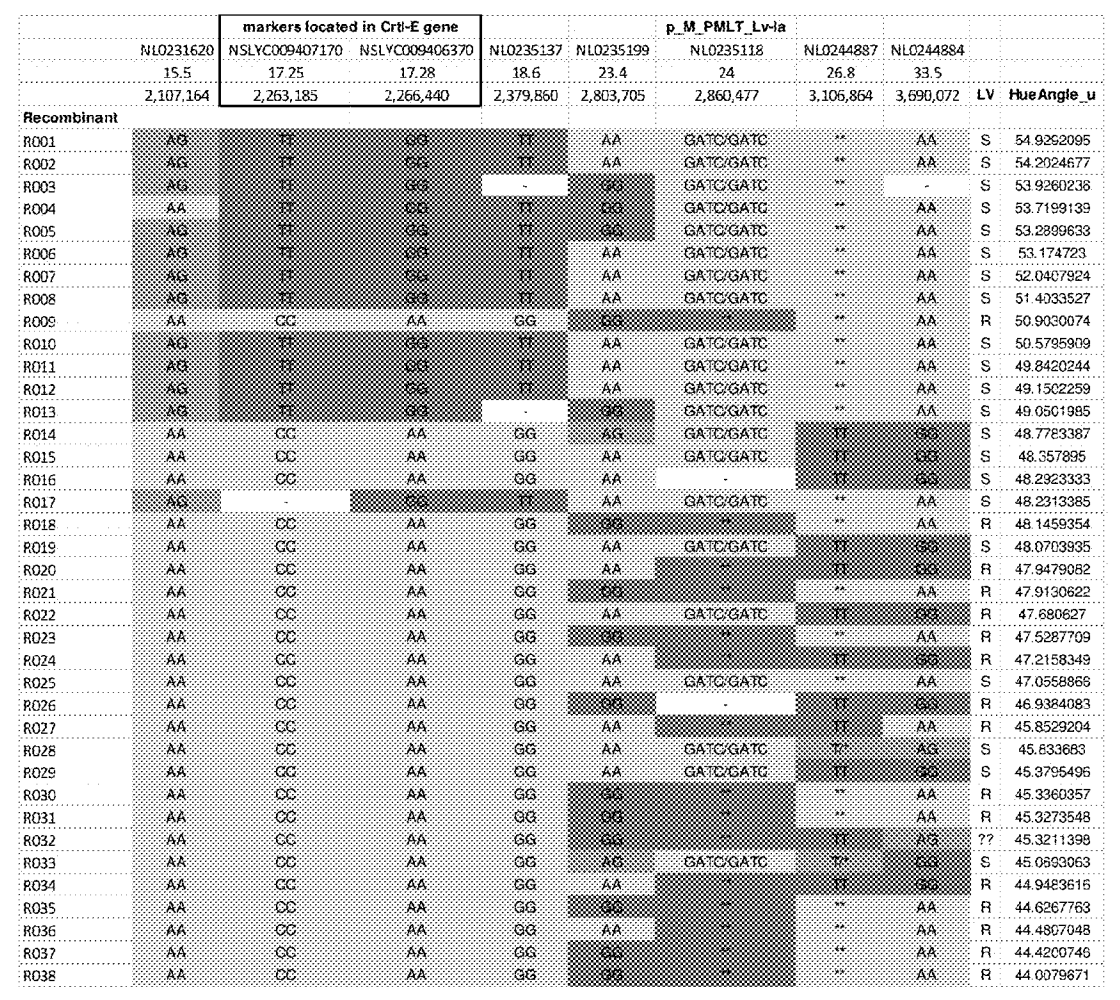

FIG. 1 shows the marker genotypes of each recombinant inbred line in the experiment, as well as the resistance scores and LSM estimate of hue angle. Markers shaded light grey are derived from Lt susceptible parent line FIR-16-2063, while markers shaded dark grey are derived from Lt resistant parent line FIR-16-2138.

FIG. 2 shows six recombinant inbred lines in which resistance to Lt was retained and unfavorable orange fruit exocarp color caused by Delta was eliminated. The recombination events in these lines are novel and extremely useful for breeding, since they represent elimination of unfavorable cis-linkage between Delta and Lt resistance QTL. Markers shaded light grey are derived from Lt susceptible parent line FIR-16-2063, while markers shaded dark grey are derived from Lt resistant parent line FIR-16-2138. Minimal efficacious resistance introgressions not exhibiting unfavorable exocarp color, were produced by identifying individuals with recombination breakpoints between SNP markers NL0235137 and NL0244887, selecting for alleles derived from Lt resistant parent line FIR-16-2138 at loci NL0235199 and NL0235118 and for alleles derived from Lt susceptible parent line FIR-16-2063 at markers NL0235137 and NL0244887, as shown in FIG. 2.

Example 4

Mapping of Fruit Exocarp Color Loci within the Lt Introgression on Chromosome 12

Using molecular markers, double recombination events were generated across the Lt resistance QTL interval in a cross of FIR-16-2063/FIR-16-2138, which have a near isogenic background outside of the Lt resistance introgression. Each double recombinant carried a unique fragment of the original 'Laurica' introgression. The original introgression size was ~15 cM, while the introgression sizes in the double recombinants ranged from ~3 to ~10 cM (FIG. 3).

Double-recombinant near isogenic lines (NILs) were testcrossed to tomato line FDR-15-2031 to recapitulate the hybrid phenotype for analysis. Double-recombinant derived hybrids were assessed in field trials in a randomized complete block design with 5 replications. Maturing fruits were tagged at breaker stage within each replication and analyzed for color 7 days later with a Konica-Minolta colorimeter to quantitatively assess their color. Phenotypic data for Lt resistance was collected in the field at the end of the season. Collected data was analyzed with a mixed model ANOVA to calculate least-squared mean estimates of fruit color, as measured by hue angle. Table 3 shows data indicating a large, heritable, and highly significant difference in fruit color between FIR-16-2063/FDR-15-2031 and FIR-16-2138/FDR-15-2031 tomato plants.

TABLE 3

Statistical data for fruit color.

| Hybrid Tomato Lines | | Delta | P-Value | Lower | Upper |
|---|---|---|---|---|---|
| FIR-16-2063/ FDR-15-2031 (red fruit exocarp color) | FIR-16-2138/ FDR-15-2031 (orange fruit exocarp color) | 10.40 | 0.00 | 8.85 | 11.96 |

A candidate gene on chromosome 12, which encodes a lycopene epsilon cyclase (Crtl-E) (*Plant J* 17(4):341, 1999) was used to create two molecular markers in Crtl-E to assay the NILs. Crtl-E is located at a position of 2.2853 to 2.2857 Mbp. Genotyping was also done with markers previously used for recombinant identification, in addition to the current trait-associated assay for Lt resistance. Genotyping results for the double recombinant progeny of FIR-16-2063/FIR-16-2138 compared to Lt susceptible FIR-16-2063/FDR-15-2031 commercial variety and resistant converted hybrid FIR-16-2138/FDR-15-2031 are shown in FIG. 4.

Example 5

Fine Mapping to Identify Minimal Efficacious Introgression

Figure 5:
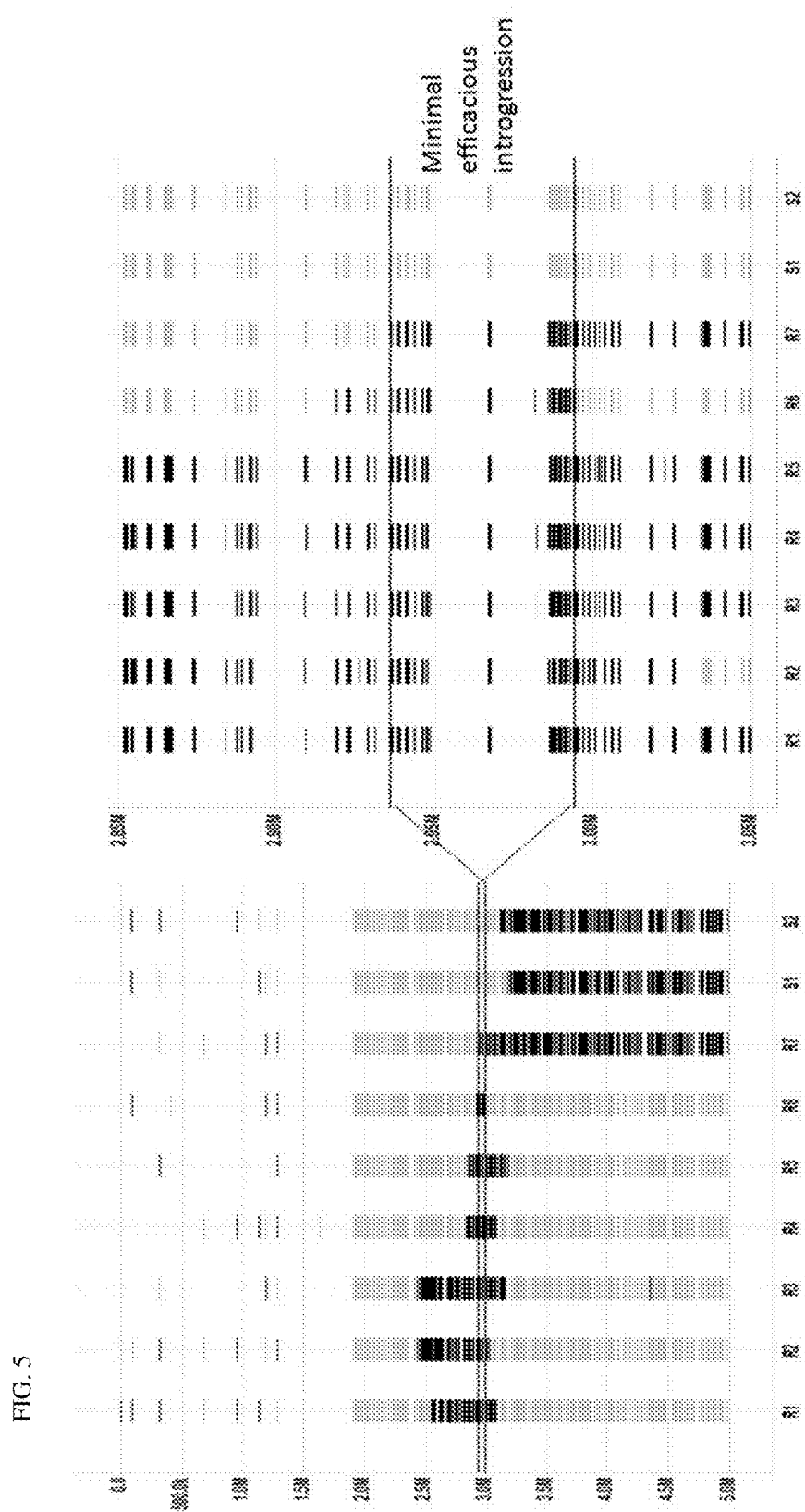
FIG. 5: Shows sequence capture data for double recombinant progeny of FIR-16-2063/FIR-16-2138. eSNPs detected within the NIL capture data are colored according to their allele origin: R parent (FIR-16-2138) alleles are shaded black and S parent (FIR-16-2063) alleles are shaded grey.

Trait association was assessed using the newly identified molecular markers in combination with field data on fruit color. NILs with lighter colored/orange fruits were found to be disproportionately enriched for the *L. chilense* introgression segments at Crtl-E gene markers (F=64.4, p<0.0001). The 7 resistant NILs shown in FIG. 4 were selected because they exhibited a hybrid fruit color closely matched to that of susceptible hybrid FIR-16-2063/FDR-15-2031 and breakpoints close to the current Lt trait-linked marker (FIG. 4). These NILs were subjected to sequence capture for high resolution mapping (FIG. 5). Sequence capture is a method for performing targeted sequencing with next generation technology. Custom target design services and reagents are available from Roche NimbleGen.

Figure 6:
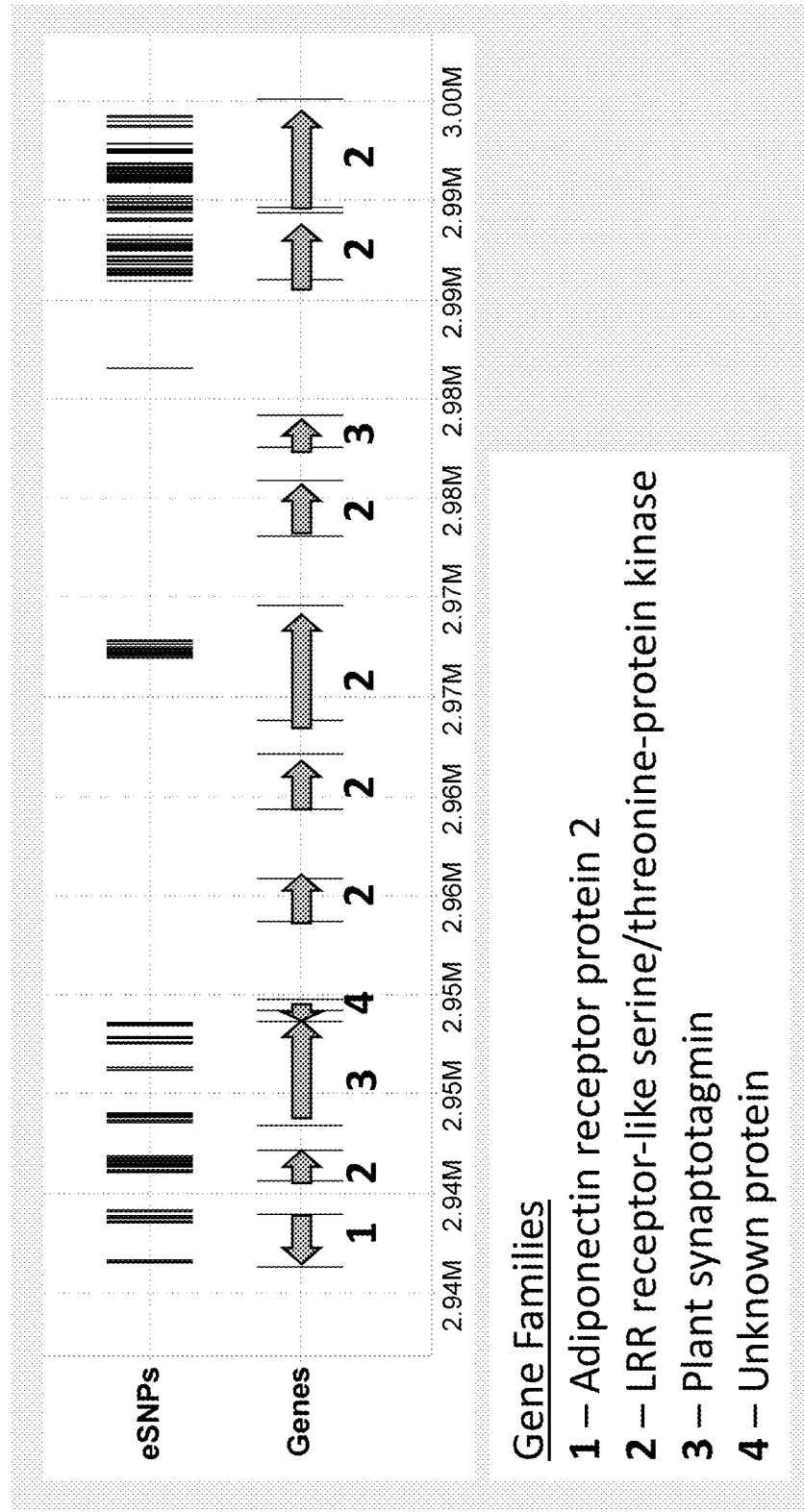
FIG. 6: Shows annotated genes in the minimal efficacious introgression provided by the invention.

High resolution sequence capture data enabled fine mapping of the recombination breakpoints between resistant NILs R6 and R7 (Tables 4 and 5). A minimal efficacious interval of 63.1 Kb (0.75 cM) conferring Lt resistance (highlighted by horizontal lines) was identified downstream of the current trait-linked Infinium marker and is defined by genomic positions 2,931,412 and 2,994,502. The minimal introgression conferring both Lt resistance and lack of undesirable orange fruit color observed was in NIL R6 and is defined by genomic positions 2,909,303 Mbp and 2,994,502 Mbp. An additional efficacious introgression fragment was shown to be defined by genomic positions 2,421,661 and 3,196,154. Within the minimal efficacious introgression, there are 225 eSNPs that are in complete linkage disequilibrium with Lt resistance across the NILs. FIG. 6 shows the locations of these eSNPs and annotated genes within the minimal efficacious introgression. These SNPs can be used in TaqMan assays for use in marker-assisted selection (MAS) breeding programs. Selection of Lt resistance without orange fruit exocarp color in these breeding events is enabled with Q-NL0235118 (p_M_PMLT_Lv-La). Table 6 provides genotypes and left and right flanking sequence (+/−150 bp) for each NIL, along with reference sequences.

TABLE 4

Introgression breakpoint intervals for 7 resistant NILs.

| Recombinant | Physical Position | Genetic Position | RIL Allele type | Breakpoint 'type' |
|---|---|---|---|---|
| R1 | 2,551,673 | 26.7 | esculentum (FIR-16-2063) | top |
| R1 | 2,551,723 | 26.7 | chilense (FIR-16-2138) | top |
| R1 | 3,077,384 | 33.2 | chilense (FIR-16-2138) | bottom |
| R1 | 3,096,032 | 33.5 | esculentum (FIR-16-2063) | bottom |
| R2 | 2,421,661 | 25.2 | esculentum (FIR-16-2063) | top |

TABLE 4-continued

Introgression breakpoint intervals for 7 resistant NILs.

| Recombinant | Physical Position | Genetic Position | RIL Allele type | Breakpoint 'type' |
|---|---|---|---|---|
| R2 | 2,436,550 | 25.4 | chilense (FIR-16-2138) | top |
| R2 | 3,025,938 | 32.5 | chilense (FIR-16-2138) | bottom |
| R2 | 3,034,301 | 32.6 | esculentum (FIR-16-2063) | bottom |
| R3 | 2,421,661 | 25.2 | esculentum (FIR-16-2063) | top |
| R3 | 2,436,561 | 25.4 | chilense (FIR-16-2138) | top |
| R3 | 3,152,613 | 34.1 | chilense (FIR-16-2138) | bottom |
| R3 | 3,180,676 | 34.5 | esculentum (FIR-16-2063) | bottom |
| R4 | 2,929,039 | 31.2 | esculentum (FIR-16-2063) | top |
| R4 | 2,929,067 | 31.2 | chilense (FIR-16-2138) | top |
| R4 | 3,041,836 | 32.7 | chilense (FIR-16-2138) | bottom |
| R4 | 3,041,866 | 32.7 | esculentum (FIR-16-2063) | bottom |
| R5 | 2,846,106 | 30.2 | esculentum (FIR-16-2063) | top |
| R5 | 2,851,881 | 30.2 | chilense (FIR-16-2138) | top |
| R5 | 3,181,352 | 34.5 | chilense (FIR-16-2138) | bottom |
| R5 | 3,196,154 | 34.7 | esculentum (FIR-16-2063) | bottom |
| R6 | 2,909,303 | 30.9 | esculentum (FIR-16-2063) | top |
| R6 | 2,918,977 | 31.1 | chilense (FIR-16-2138) | top |
| R6 | 2,994,248 | 32 | chilense (FIR-16-2138) | bottom |
| R6 | 2,994,502 | 32 | esculentum (FIR-16-2063) | bottom |
| R7 | 2,931,412 | 31.2 | esculentum (FIR-16-2063) | top |
| R7 | 2,936,184 | 31.3 | chilense (FIR-16-2138) | top |

TABLE 5

Sequence capture data for 7 resistant NILs compared to reference sequence (Solanum lycopersicum_Heinz 1706_ITAG_V2.3).

| Recombinant | Position | Left Flanking Sequence (SEQ ID NO) | Genotype | Right Flanking Sequence (SEQ ID NO) |
|---|---|---|---|---|
| Reference | 2,551,673 | 1 | [C/C] | 53 |
| R1 | 2,551,673 | 2 | [C/C] | 54 |
| Reference | 2,551,723 | 3 | [A/A] | 55 |
| R1 | 2,551,723 | 4 | [T/T] | 56 |
| Reference | 3,077,384 | 5 | [C/C] | 57 |
| R1 | 3,077,384 | 6 | [A/A] | 58 |
| Reference | 3,096,032 | 7 | [G/G] | 59 |
| R1 | 3,096,032 | 8 | [G/G] | 60 |
| Reference | 2,421,661 | 9 | [C/C] | 61 |
| R2 | 2,421,661 | 10 | [C/C] | 62 |
| Reference | 2,436,550 | 11 | [A/A] | 63 |
| R2 | 2,436,550 | 12 | [G/G] | 64 |
| Reference | 3,025,938 | 13 | [T/T] | 65 |
| R2 | 3,025,938 | 14 | [C/C] | 66 |
| Reference | 3,034,301 | 15 | [A/A] | 67 |
| R2 | 3,034,301 | 16 | [A/A] | 68 |
| Reference | 2,421,661 | 17 | [C/C] | 69 |
| R3 | 2,421,661 | 18 | [C/C] | 70 |
| Reference | 2,436,561 | 19 | [g/g] | 71 |
| R3 | 2,436,561 | 20 | [A/A] | 72 |
| Reference | 3,152,613 | 21 | [A/A] | 73 |
| R3 | 3,152,613 | 22 | [G/G] | 74 |
| Reference | 3,180,676 | 23 | [C/C] | 75 |
| R3 | 3,180,676 | 24 | [C/C] | 76 |
| Reference | 2,929,039 | 25 | [T/T] | 77 |
| R4 | 2,929,039 | 26 | [T/T] | 78 |
| Reference | 2,929,067 | 27 | [G/G] | 79 |
| R4 | 2,929,067 | 28 | [A/A] | 80 |
| Reference | 3,041,836 | 29 | [A/A] | 81 |
| R4 | 3,041,836 | 30 | [G/G] | 82 |
| Reference | 3,041,866 | 31 | [T/T] | 83 |
| R4 | 3,041,866 | 32 | [T/T] | 88 |
| Reference | 2,846,106 | 33 | [A/A] | 85 |
| R5 | 2,846,106 | 34 | [A/A] | 86 |
| Reference | 2,851,881 | 35 | [A/A] | 87 |
| R5 | 2,851,881 | 36 | [T/T] | 88 |
| Reference | 3,181,352 | 37 | [G/G] | 89 |
| R5 | 3,181,352 | 38 | [C/C] | 90 |
| Reference | 3,196,154 | 39 | [A/A] | 91 |
| R5 | 3,196,154 | 40 | [A/A] | 92 |
| Reference | 2,909,303 | 41 | [G/G] | 93 |
| R6 | 2,909,303 | 42 | [G/G] | 94 |
| Reference | 2,918,977 | 43 | [C/C] | 95 |
| R6 | 2,918,977 | 44 | [T/T] | 96 |
| Reference | 2,994,248 | 45 | [G/G] | 97 |
| R6 | 2,994,248 | 46 | [A/A] | 98 |
| Reference | 2,994,502 | 47 | [G/G] | 99 |
| R6 | 2,994,502 | 48 | [G/G] | 100 |
| Reference | 2,931,412 | 49 | [G/G] | 101 |
| R7 | 2,931,412 | 50 | [G/G] | 102 |
| Reference | 2,936,184 | 51 | [T/T] | 103 |
| R7 | 2,936,184 | 52 | [C/C] | 104 |

TABLE 6

Sequences for molecular markers on tomato chromosome 12 useful for tracking the Lt resistance QTL in tomato.

| Marker Name | Position | Alleles | VIC Sequence (SEQ ID NO) | FAM Sequence (SEQ ID NO) | F Sequence (SEQ ID NO) | R Sequence (SEQ ID NO) | Trait Locus Name |
|---|---|---|---|---|---|---|---|
| Q-NL0235118 | 31.1 | GATC/**** | 105 | 109 | 113 | 117 | p_M_PMLT_Lv-La |
| Q-NL0235137 | 25.21 | G/T | 106 | 110 | 114 | 118 | |
| Q-NL0235199 | 30.39 | G/A | 107 | 111 | 115 | 119 | |
| Q-NL0244887 | 34.69 | T/* | 108 | 112 | 116 | 120 | |

Example 6

Selection of Desired Recombinants

Classification of "orange" versus "red" is important relative to the checks FIR-16-2063/FDR-15-2031 and FIR-16-2138/FDR-15-2031 because FIR-16-2138/FDR-15-2031 is a standard for unacceptable orange fruit color, while FIR-16-2063/FDR-15-2031 is a standard for acceptable red fruit color. A significant reason that FIR-16-2138/FDR-15-2031 exhibits this unacceptable orange color is due to the close linkage of the Del mutation 500 Kb upstream of the Lt resistance locus. By computing the means and confidence intervals around the various classes of recombinants shown in FIG. 1 of the patent application, it becomes easier to classify "orange" and "red" quantitatively. Table 7 provides means and standard errors calculated from 2013 and 2014 field data as described herein.

Recombinants that continue to carry the *S. chilense* allele at the Del locus exhibit a LSM hue angle of 51.39343±0.41802, which closely mirrors the value computed for the FIR-16-2138/FDR-15-2031 check. Contrastingly, recombinants wherein the *S. chilense* allele at this locus has been replaced with a *S. esculentum* allele exhibit a LSM hue angle of 46.963±0.39518, which more closely approximates the value computed for the FIR-16-2063/FDR-15-2031 check. Accordingly, any recombinants that have retained resistance and eliminated the *S. chilense* allele at the Del locus may be useful, particularly those that have a LSM estimate for hue angle of less than 47.35. A third group of most useful recombinants and the primary focus of the patent application are those wherein a double recombination has been created across this region, eliminating the *S. chilense* allele at the Del locus and extraneous *S. chilense* DNA downstream of physical position 3,690,072 (genetic position marker 33.5), while still retaining resistance to *Leveillula taurica*. The LSM estimate for hue angle of 44.8969±0.34424 is not statistically different than the LSM estimate and error calculated for the FIR-16-2063/FDR-15-2031 check, clearly indicating that all deleterious effect on fruit color from *S. chilense* donor DNA in this region has been eliminated and giving strong confidence that resistance for *Leveillula taurica* was retained while successfully reverting to a desirable "red" fruit color.

TABLE 7

Means and standard errors calculated from 2013 and 2014 field data as described above.

One way Anova of Hue Angle by Group
Analysis of Variance

| Source | DF | Sum of Squares | Mean Square | F Ratio | Prob > F |
|---|---|---|---|---|---|
| Crtl-E gene group | 4 | 46771.58 | 11692.9 | 315.2554 | <.0001 |
| Error | 4231 | 156928.77 | 37.1 | | |
| C. Total | 4235 | 203700.35 | | | |

Means for One way Anova

| Level | Number | Mean | Std Error | Lower 95% | Upper 95% | Classification |
|---|---|---|---|---|---|---|
| FIR-16-2063/FDR-15-2031 check | 588 | 44.1528 | 0.25115 | 43.660 | 44.645 | red |
| FIR-16-2138/FDR-15-2031 (+Lt full introgression) check | 597 | 52.5087 | 0.24925 | 52.020 | 52.997 | orange |
| Recombinants w/chilense allele at Del (Ctrl-E) gene | 849 | 51.9343 | 0.20901 | 51.525 | 52.344 | orange |
| Recombinants w/esculentum allele at Del (Ctrl-E) gene | 950 | 46.9630 | 0.19759 | 46.576 | 47.350 | red |
| Double recombinant progeny - esculentum allele at Ctrl-E and downstream of 3,690,072 (genetic position marker 33.5) | 1252 | 44.8969 | 0.17212 | 44.559 | 45.234 | red |

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A tomato plant of a cultivated tomato plant variety comprising a recombinant introgression from *Solanum chilense* on chromosome 12, wherein said recombinant introgression comprises a first allele conferring improved resistance to *Leveillula taurica* (Lt) relative to a plant lacking said first allele, and wherein said recombinant introgression lacks a second allele from *Solanum chilense* genetically linked to said first allele, wherein the second allele would confer orange fruit exocarp if present in said recombinant introgression, and wherein said first allele comprises alleles from *Solanum chilense* at locus NL0235199 and at locus NL0235118 and said second allele lacks alleles from *Solanum chilense* at locus NL0235137 and at locus NL0244887.

2. The tomato plant of claim 1, wherein the plant comprises *Solanum chilense* donor DNA between approximately 2.42 Mbp and 3.19 Mbp on chromosome 12.

3. The tomato plant of claim 2, wherein the plant comprises *Solanum chilense* donor DNA between approximately 2.93 Mbp and 2.99 Mbp on chromosome 12.

4. The tomato plant of claim 1, wherein the plant comprises *Solanum chilense* donor DNA between approximately: 2.55 Mbp and 3.09 Mbp; 2.42 Mbp and 3.03 Mbp; 2.42 Mbp and 3.18 Mbp; 2.85 Mbp and 3.09 Mbp; 2.85 Mbp and 3.19 Mbp; 2.91 Mbp and 2.99 Mbp; or 2.93 Mbp and 5.47 Mbp on chromosome 12.

5. The tomato plant of claim 4, wherein the plant comprises *Solanum chilense* donor DNA between approximately: 2.85 Mbp and 3.09 Mbp; 2.85 Mbp and 3.19 Mbp; or 2.91 Mbp and 2.99 Mbp on chromosome 12.

6. The tomato plant of claim 1, wherein said second allele is located in the genomic region encoding Crtl-E.

7. The tomato plant of claim 1, wherein the plant comprises *S. chilense* donor DNA within a genomic segment flanked by NL0235137 and NL0244887.

8. A plant part of the plant of claim 1, wherein the plant part comprises said recombinant introgression.

9. The plant part of claim 8, wherein the plant part is a cell, a seed, a root, a stem, a leaf, a fruit, a flower, or pollen.

10. A method for producing a tomato plant having improved resistance to *Leveillula taurica* (Lt) and lacking an orange fruit exocarp color, said method comprising:

a) crossing the tomato plant of claim 1 with itself or with a second tomato plant of a different genotype to produce one or more progeny plants; and b) selecting a progeny plant comprising said recombinant introgression.

11. The method of claim 10, wherein selecting said progeny plant comprises identifying a progeny plant that (1) comprises a *Solanum chilense* allele at a locus genetically linked to said first allele and/or lacks an allele present at the corresponding locus in the cultivated tomato plant variety, and (2) lacks a *Solanum chilense* allele at a locus genetically linked to said second allele that confers orange fruit exocarp color, and/or comprises an allele present at the corresponding locus from the cultivated tomato plant variety.

12. The method of claim 11, wherein selecting said progeny plant comprises marker-assisted selection (MAS).

13. The method of claim 12, wherein marker-assisted selection (MAS) comprises detecting at least one allele at a locus located between approximately 2.42 Mbp and 3.19 Mbp on chromosome 12.

14. The method of claim 13, wherein marker-assisted selection (MAS) comprises detecting at least one allele at a locus located between approximately 2.93 Mbp and 2.99 Mbp on chromosome 12.

15. The method of claim 12, wherein marker-assisted selection (MAS) comprises detecting at least one allele at a locus selected from the group consisting of NL0235199, NL0235118, NL0235137, and NL0244887.

16. The method of claim 10, wherein the progeny plant is an F2-F6 progeny plant.

17. The method of claim 10, wherein producing the progeny plant comprises backcrossing.

18. The method of claim 17, wherein backcrossing comprises from 2-7 generations of backcrossing.

19. A method for obtaining a tomato plant exhibiting improved resistance to *Leveillula taurica* (Lt) comprising:
(a) obtaining a tomato plant heterozygous for a first allele that confers resistance to *Leveillula taurica* (Lt) and that is genetically linked in the plant to a second allele from *Solanum chilense* that confers orange fruit exocarp color;
(b) crossing the plant of step (a) with itself or a second tomato plant to produce progeny of the plant of step (a); and
(c) selecting at least a first progeny plant in which recombination has occurred such that the progeny comprises a recombinant introgression from *Solanum chilense* on chromosome 12, wherein said recombinant introgression comprises a first allele conferring improved resistance to *Leveillula taurica* (Lt) relative to a plant lacking said first allele, and wherein said recombinant introgression lacks a second allele from *Solanum chilense* that would confer orange fruit exocarp if present in said recombinant introgression, and wherein said first allele comprises alleles from *Solanum chilense* at locus NL0235199 and at locus NL0235118 and said second allele lacks alleles from *Solanum chilense* at locus NL0235137 and at locus NL0244887.

20. The method of claim 19, wherein selecting said first progeny comprises detecting at least one allele at a locus located between approximately 2.93 Mbp and 2.99 Mbp on chromosome 12.

21. The method of claim 19, wherein selecting said first progeny comprises detecting at least one allele at a locus selected from the group consisting of NL0235199, NL0235118, NL0235137, and NL0244887.

22. The method of claim 19, wherein said progeny plant is an F2-F6 progeny plant.

23. The method of claim 19, wherein obtaining said progeny plant comprises backcrossing.

24. The method of claim 23, wherein backcrossing comprises from 2-7 generations of backcrossing.

25. A plant produced by the method of claim 19, wherein the plant comprises said recombinant introgression.

26. A part of the plant of claim 25, selected from the group consisting of a cell, a seed, a root, a stem, a leaf, a fruit, a flower, and pollen, wherein the plant part comprises said recombinant introgression.

* * * * *

SEQUENCE LISTING

<160> NUMBER OF SEQ ID NOS: 120

<210> SEQ ID NO 1
<211> LENGTH: 150
<212> TYPE: DNA
<213> ORGANISM: Solanum lycopersicum

<400> SEQUENCE: 1

```
tgtcatgatt ttgaacatcg aggacgaatg atgaaattta cagtatcaag ataagtgttt    60
gatacgatga aaaatctttc ttaataaata ttttatctga acaaggggct agaaaaatga   120
tttctctcac gtacgaatga aaatcatttt                                    150
```

<210> SEQ ID NO 2
<211> LENGTH: 150
<212> TYPE: DNA
<213> ORGANISM: Solanum lycopersicum

<400> SEQUENCE: 2

```
tgtcatgatt ttgaacatcg aggacgaatg atgaaattta cagtatcaag ataagtgttt    60
gatacgatga aaaatctttc ttaataaata ttttatctga acaaggggct agaaaaatga   120
tttctctcac gtacgaatga aaatcatttt                                    150
```

<210> SEQ ID NO 3
<211> LENGTH: 150
<212> TYPE: DNA
<213> ORGANISM: Solanum lycopersicum

<400> SEQUENCE: 3

```
ataagtgttt gatacgatga aaaatctttc ttaataaata ttttatctga acaaggggct    60
agaaaaatga tttctctcac gtacgaatga aaatcatttt ctttataact atcttaattt   120
ttaaacttca tattaccact ccatataata                                    150
```

<210> SEQ ID NO 4
<211> LENGTH: 150
<212> TYPE: DNA
<213> ORGANISM: Solanum lycopersicum

<400> SEQUENCE: 4

```
ataagtgttt gatacgatga aaaatctttc ttaataaata ttttatctga acaaggggct    60
agaaaaatga tttctctcac gtacgaatga aaatcatttt ctttataact atcttaattt   120
ttaaacttca tattaccact ccatataata                                    150
```

<210> SEQ ID NO 5
<211> LENGTH: 150
<212> TYPE: DNA
<213> ORGANISM: Solanum lycopersicum

<400> SEQUENCE: 5

```
tctgcaacaa ttgaccatat caaccaagaa aagatctttt atcttgttat caagtttcaa    60
gttttgtata attgaaactt ttaatcaaca atgactatac agaagtatgt ttttgatatt   120
aatggttatt tagtctccta tttttttatgc                                   150
```

<210> SEQ ID NO 6
<211> LENGTH: 152
<212> TYPE: DNA
<213> ORGANISM: Solanum lycopersicum

<400> SEQUENCE: 6
```

```
tctgcaacaa ttttgaccat atcaaccaag aaaagatctt ttatcttgtt atcaagtttc      60
aagttttgta taattgaaac ttttaatcaa caatgactat acagaagtat gttttttgata    120 ttaatggtta tttagtctcc tatttttttat gc                                  152
```

<210> SEQ ID NO 7
<211> LENGTH: 150
<212> TYPE: DNA
<213> ORGANISM: Solanum lycopersicum

<400> SEQUENCE: 7

```
tcgcgatgga gagcctccga ttctagtgtt cctggaaaaa ctaacaaagc ctattaatga      60
aatatgtgtt caactctcta caaaagcaaa aagttagtc attgttcatg accttataat     120
gagtgaacaa atattggaag taaatacatt                                      150
```

<210> SEQ ID NO 8
<211> LENGTH: 150
<212> TYPE: DNA
<213> ORGANISM: Solanum lycopersicum

<400> SEQUENCE: 8

```
tcgcgatgga gagcctccga ttctagtgtt cctggaaaaa ctaacaaagc ctattaatga      60
aatatgtgtt caactctcta caaaagcaaa aagttagtc attgttcatg accttataat     120
gagtgaacaa atattggaag taaatacatt                                      150
```

<210> SEQ ID NO 9
<211> LENGTH: 150
<212> TYPE: DNA
<213> ORGANISM: Solanum lycopersicum

<400> SEQUENCE: 9

```
atcctggtac ctgtacaaca aaaggctctt agcaaaatta tcattttatc atctagaagc      60
agtggtgaaa aagatttaga agcattgaag ctttcttcca cctcttctca aaagtcctct    120
tggagggcca taaagatagt cgcattgaca                                      150
```

<210> SEQ ID NO 10
<211> LENGTH: 150
<212> TYPE: DNA
<213> ORGANISM: Solanum lycopersicum

<400> SEQUENCE: 10

```
atcctggtac ctgtacaaca aaaggctctt agcaaaatta tcattttatc atctagaagc      60
agtggtgaaa aagatttaga agcattgaag ctttcttcca cctcttctca aaagtcctct    120
tggagggcca taaagatagt cgcattgaca                                      150
```

<210> SEQ ID NO 11
<211> LENGTH: 150
<212> TYPE: DNA
<213> ORGANISM: Solanum lycopersicum

<400> SEQUENCE: 11

```
ttcttttttct tgaagtataa aaagttttaa aaatttcaaa aatatatata attaaagggt      60
aaattaataa aattattatt tttatttata attttttaaa aaatatgtaa attgaaaaat    120
agacaactaa tataaaacaa aaaatatatt                                      150
```

<210> SEQ ID NO 12

```
<211> LENGTH: 150
<212> TYPE: DNA
<213> ORGANISM: Solanum lycopersicum

<400> SEQUENCE: 12 ttcttttct tgaagtataa aaagttttaa aaatttcaaa aatatatata attaaagggt      60
aaattaataa aattattatt tttatttata atttttaaaa aaatatgtaa attgaaaaat    120
agacaactaa tataaaacaa aaaatatatt                                     150

<210> SEQ ID NO 13
<211> LENGTH: 150
<212> TYPE: DNA
<213> ORGANISM: Solanum lycopersicum

<400> SEQUENCE: 13
caacaaccaa ttatatgtga aatgtaaaaa tccaagtgtc aacctaaaga aaacgtccca     60
acattgcaga gccacgactt tcgctaagag gattcaaaat ataaacaaat agcacaaaca   120
aaccaagggg attattcatc atgtacaata                                     150

<210> SEQ ID NO 14
<211> LENGTH: 150
<212> TYPE: DNA
<213> ORGANISM: Solanum lycopersicum

<400> SEQUENCE: 14
caacaaccaa ttatatgtga aatgtaaaaa tataagtgtc aacctaaaga aaacgtccca     60
acattgcaga gccacgactt tcaccaagag gattcaaaat ataaacaaat agcacaaaca   120
aaccaagggg attattcatc atgtactata                                     150

<210> SEQ ID NO 15
<211> LENGTH: 150
<212> TYPE: DNA
<213> ORGANISM: Solanum lycopersicum

<400> SEQUENCE: 15
atgctctggt atactctctc tgtactttac atggtttgtc ggtatacttt cttctgattt     60
acttggcgtt tttagcattt gactgttaaa gatctaagct tttcctgctt tgtgtgttgc   120
ttactagtta aataatgatt attttaacac                                     150

<210> SEQ ID NO 16
<211> LENGTH: 150
<212> TYPE: DNA
<213> ORGANISM: Solanum lycopersicum

<400> SEQUENCE: 16
atgctctggt atactctctc tgtactttac atggtttgtc ggtatacttt cttctgattt     60
acttggcgtt tttagcattt gactgttaaa gatctaagct tttcctgctt tgtgtgttgc   120
ttactagtta aataatgatt attttaacac                                     150

<210> SEQ ID NO 17
<211> LENGTH: 150
<212> TYPE: DNA
<213> ORGANISM: Solanum lycopersicum

<400> SEQUENCE: 17
atcctggtac ctgtacaaca aaaggctctt agcaaaatta tcattttatc atctagaagc     60
agtggtgaaa aagatttaga agcattgaag ctttcttcca cctcttctca aaagtcctct   120
```

```
tggagggcca taaagatagt cgcattgaca                                    150

<210> SEQ ID NO 18
<211> LENGTH: 150
<212> TYPE: DNA
<213> ORGANISM: Solanum lycopersicum

<400> SEQUENCE: 18
atcctggtac ctgtacaaca aaaggctctt agcaaaatta tcattttatc atctagaagc    60
agtggtgaaa aagatttaga agcattgaag ctttcttcca cctcttctca aaagtcctct   120
tggagggcca taaagatagt cgcattgaca                                    150

<210> SEQ ID NO 19
<211> LENGTH: 150
<212> TYPE: DNA
<213> ORGANISM: Solanum lycopersicum

<400> SEQUENCE: 19
gaagtataaa aagttttaaa aatttcaaaa atatatataa ttaaagggta aattaataaa    60
attattattt ttatttataa ttttttaaaa aatatgtaaa ttgaaaaata gacaactaat   120
ataaaacaaa aaatatatta atttacttaa                                    150

<210> SEQ ID NO 20
<211> LENGTH: 150
<212> TYPE: DNA
<213> ORGANISM: Solanum lycopersicum

<400> SEQUENCE: 20
gaagtataaa aagttttaaa aatttcaaaa atatatataa ttaaagggta aattaataaa    60
attattattt ttatttataa ttttttaaaa aatatgtaaa ttgaaaaata gacaactaat   120
ataaaacaaa aaatatattg atttacttaa                                    150

<210> SEQ ID NO 21
<211> LENGTH: 150
<212> TYPE: DNA
<213> ORGANISM: Solanum lycopersicum

<400> SEQUENCE: 21
aagcagagta gacgtacaac gtgtaccaaa caaagaatag agtcacaaac aaatatacca    60
gcaactgaag gtccaagagc aaccataata gcaccagtta atgttgccag atcaattatc   120
tgcataaatt caatcagtga atcaggggaa                                    150

<210> SEQ ID NO 22
<211> LENGTH: 150
<212> TYPE: DNA
<213> ORGANISM: Solanum lycopersicum

<400> SEQUENCE: 22
aagcagagta cacgtacaac gtgtaccaaa caaagaatag agtcacaaac aaatatacca    60
gcaactgaag gtccaagagc aaccataata gcaccagtta atgttgccag atcaattatc   120
tgcataaatt caatcagtga atcaggggaa                                    150

<210> SEQ ID NO 23
<211> LENGTH: 150
<212> TYPE: DNA
<213> ORGANISM: Solanum lycopersicum
```

<400> SEQUENCE: 23
aggtggatat acgttagtcg tgttgatgtc atgaacacta ctcattttag aatgtcgatc    60
tttagaatca ccttcaagtt tacctactat ggtaccacag tgaatacgat ctctaccaga   120
catgcatgaa taggataggg gtaataaatt                                    150

<210> SEQ ID NO 24
<211> LENGTH: 150
<212> TYPE: DNA
<213> ORGANISM: Solanum lycopersicum

<400> SEQUENCE: 24
aggtggatat acgttagtcg tgttgatgtc atgaacacta ctcattttag aatgtcgatc    60
tttagaatca ccttcaagtt tacctactat ggtaccacag tgaatacgat ctctaccaga   120
catgcatgaa taggataggg gtaataaatt                                    150

<210> SEQ ID NO 25
<211> LENGTH: 150
<212> TYPE: DNA
<213> ORGANISM: Solanum lycopersicum

<400> SEQUENCE: 25 tacgttttaaa aaaatacaa atttcttata aagtctatcg acaattagct tttcgataac    60
aattctgata gactttcct tgaaaatctc agttaatgtg aatgctcatt gaaaattcac   120
gttttttaaa tagctagtta attaacttaa                                    150

<210> SEQ ID NO 26
<211> LENGTH: 150
<212> TYPE: DNA
<213> ORGANISM: Solanum lycopersicum

<400> SEQUENCE: 26 tacgttttaaa aaaatacaa atttctwata aagtgtattg acaattagct tttcgataac    60
aattctgata gactcttcat tgaaaatctc agttaatgtg aatgctcatt gaaaattcac   120 gtttttaag tagctagtta attaacttaa                                    150

<210> SEQ ID NO 27
<211> LENGTH: 150
<212> TYPE: DNA
<213> ORGANISM: Solanum lycopersicum

<400> SEQUENCE: 27
taaagtctat cgacaattag cttttcgata acaattctga tagactttc tttgaaaatc    60 tcagttaatg tgaatgctca ttgaaaattc acgttttta aatagctagt taattaactt   120
aatgtttgta taaaaaatat ttacattatc                                    150

<210> SEQ ID NO 28
<211> LENGTH: 150
<212> TYPE: DNA
<213> ORGANISM: Solanum lycopersicum

<400> SEQUENCE: 28
taaagtgtat tgacaattag cttttcgata acaattctga tagactcttc attgaaaatc    60
tcagttaatg tgaatgctca ttgaaaattc acgttttta agtagctagt taattaactt   120
aatgtttgta taaaaaatat ttacattatc                                    150

```
<210> SEQ ID NO 29
<211> LENGTH: 150
<212> TYPE: DNA
<213> ORGANISM: Solanum lycopersicum

<400> SEQUENCE: 29
gagcaaaaca atataaataa tcttctctgt aattccctca acaagtacac accttattaa      60
catataatac ctaaagttag cagcttgggg aacaaacact aacatacaac aacataccccc   120 gtgtaatccc acaagtcggg cctagagagg                                     150

<210> SEQ ID NO 30
<211> LENGTH: 150
<212> TYPE: DNA
<213> ORGANISM: Solanum lycopersicum

<400> SEQUENCE: 30
gagcaaaaca atataaataa tcttctgtat aattccctca acaagaacac accttattaa     60
catataatac ctacagttag cagcttgggg aacaaacact aacatacaac aacataccct    120
gtgtaatcct acaagtccgg tctagggagg                                     150

<210> SEQ ID NO 31
<211> LENGTH: 150
<212> TYPE: DNA
<213> ORGANISM: Solanum lycopersicum

<400> SEQUENCE: 31
aattccctca acaagtacac accttattaa catataatac ctaaagttag cagcttgggg     60
aacaaacact aacatacaac aacataccccc gtgtaatccc acaagtcggg cctagagagg   120
atagtgtgta cgcaaaacct taaccctacc                                     150

<210> SEQ ID NO 32
<211> LENGTH: 150
<212> TYPE: DNA
<213> ORGANISM: Solanum lycopersicum

<400> SEQUENCE: 32
aattccctca acaagaacac accttattaa catataatac ctacagttag cagcttgggg     60
aacaaacact aacatacaac aacataccct gtgtaatcct acaagtccgg tctagggagg    120
gtagtgtgta cgcaaaacct taaccctacc                                     150

<210> SEQ ID NO 33
<211> LENGTH: 150
<212> TYPE: DNA
<213> ORGANISM: Solanum lycopersicum

<400> SEQUENCE: 33
ttacttttaa tacgagatat attacgctga atctcatatt ttaaggaggt ttatttataa     60
attatgttac gtagataaat ataatgtatg actcagaatc tcgttgtaca taggctttct    120
ctttactaga atgatttaga ctataatatg                                     150

<210> SEQ ID NO 34
<211> LENGTH: 150
<212> TYPE: DNA
<213> ORGANISM: Solanum lycopersicum

<400> SEQUENCE: 34
ttacttttaa tacgagatat attacgctga atctcatatt ttaaggaggt ttatttataa     60
```

```
attatgttac gtagataaat ataatgtatg actcagaatc tcgttgtaca taggctttct    120
ctttactaga atgatttaga ctataatatg                                     150

<210> SEQ ID NO 35
<211> LENGTH: 150
<212> TYPE: DNA
<213> ORGANISM: Solanum lycopersicum

<400> SEQUENCE: 35
ctataaatgg tgaagaaaat cagttaactg ccagtttagg caagaaaaaa aaagattaaa    60
aaaaattgtg attaaaaaaa aaatttgtaa aaatgacacg tgtcataatc agatggattg    120
acaagtaatc ctagcccttg aaatctatta                                     150

<210> SEQ ID NO 36
<211> LENGTH: 150
<212> TYPE: DNA
<213> ORGANISM: Solanum lycopersicum

<400> SEQUENCE: 36
ctataaatgg tgaagaaaat cagttaactg ccagtttagg caagaaaaaa aaagattaaa    60
aaaaattgtg attaaaaaaa aaatttgtaa aaatgacacg tgtcataatc agatggattg    120
acaagtaatc ctagcccttg aaatctatta                                     150

<210> SEQ ID NO 37
<211> LENGTH: 150
<212> TYPE: DNA
<213> ORGANISM: Solanum lycopersicum

<400> SEQUENCE: 37
tcgtcacttt tattctgttt atgatgtaag aagaaacttt tggctctact aaacataagc    60
ttgcattgct gctagaacag aaagtccaga tcattttgt tcctccaaaa gtagtaactc     120
cctcagtttc gatttgtttg ttttactttt                                     150

<210> SEQ ID NO 38
<211> LENGTH: 151
<212> TYPE: DNA
<213> ORGANISM: Solanum lycopersicum

<400> SEQUENCE: 38
tcgtcacttt tattctgttt atgatctaag aagaaacttt tggctctact aaacataagc    60
tttgcattgc tgctagaaca gaaagtccag atcattttg ttcctccaaa agtagtaact    120
ccctcagttt cgatttgttt gtgttacttt c                                   151

<210> SEQ ID NO 39
<211> LENGTH: 150
<212> TYPE: DNA
<213> ORGANISM: Solanum lycopersicum

<400> SEQUENCE: 39 gatttttac gtacattctt tcaccttgta tccaacactt ctataatctt atataagaaa     60 aaaaaaatg acaaccaatt caaattactc accaacaaaa attttcattt ccgctcaaaa    120
ccttaatctt ttcaaaaatt tatacgacat                                     150

<210> SEQ ID NO 40
<211> LENGTH: 150
<212> TYPE: DNA
<213> ORGANISM: Solanum lycopersicum
```

<400> SEQUENCE: 40
gattttttac gtacattctt tcaccttgta tccaacactt ctataatctt atataagaaa        60
aaaaaaaatg acaaccaatt caaattactc accaacaaaa attttcattt ccgctcaaaa       120
ccttaatctt ttcaaaaatt tatacgacat                                        150

<210> SEQ ID NO 41
<211> LENGTH: 150
<212> TYPE: DNA
<213> ORGANISM: Solanum lycopersicum

<400> SEQUENCE: 41
acaaatttga ttcgattcat tcgatgtttt ttaaaatagt tttttattgt gaataaaaat        60
aaaatgagga caaatcaat atataagaca cttaaaagat ttaaaaccat gttaagtgat       120
gatgtgtctc gccataaaaa tgcgtaaaac                                        150

<210> SEQ ID NO 42
<211> LENGTH: 150
<212> TYPE: DNA
<213> ORGANISM: Solanum lycopersicum

<400> SEQUENCE: 42
acaaatttga ttcgattcat tcgatgtttt ttaaaatagt tttttattgt gaataaaaat        60
aaaatgagga caaatcaat atataagaca cttaaaagat ttaaaaccat gttaagtgat       120
gatgtgtctc gccataaaaa tgcgtaaaac                                        150

<210> SEQ ID NO 43
<211> LENGTH: 150
<212> TYPE: DNA
<213> ORGANISM: Solanum lycopersicum

<400> SEQUENCE: 43
tgcctgggcg tatctgctta acgctagata tgtggtcctc ctgctacact gtgggctatg        60
tgttcataac cgggcagtat attgacagtg agtggaaaat tcacaggaaa atactcaata       120
tcattatgga accatatcca gattctgaca                                        150

<210> SEQ ID NO 44
<211> LENGTH: 150
<212> TYPE: DNA
<213> ORGANISM: Solanum lycopersicum

<400> SEQUENCE: 44
tgcctgggcg tatctgctta acgctagata tgtggtcctc ctgctacact gtgggctatg        60
tgttcataac cgggcagtat attgacagtg agtggaaaat tcacaggaaa atactcaata       120
tcattatgga accatatcca gattctgaca                                        150

<210> SEQ ID NO 45
<211> LENGTH: 150
<212> TYPE: DNA
<213> ORGANISM: Solanum lycopersicum

<400> SEQUENCE: 45
tcttgtaaat ggtaatcgat ttgaaggaac tgttccaatg tcattactca actgttttcg        60
tttagaaatc tttgatgtgg gtaacaacgc tataaatgac acatttccag cttggctcgg       120
aatgcttcaa gagctgcagg tccttatatt                                        150

```
<210> SEQ ID NO 46
<211> LENGTH: 150
<212> TYPE: DNA
<213> ORGANISM: Solanum lycopersicum

<400> SEQUENCE: 46
tcttgtaaat ggtaatcgat ttgaaggaac tgttccaatg tcattactca actgttttcg      60
tttagaaatc tttgatgtgg gtaacaacgc tataaatgat acatttccag cttggctcgg     120
aatgcttcaa gagctgcagg tccttatttt                                      150

<210> SEQ ID NO 47
<211> LENGTH: 150
<212> TYPE: DNA
<213> ORGANISM: Solanum lycopersicum

<400> SEQUENCE: 47
ctgcaagact ttttgagaac ttcagtgcga tgattaaatt agatgacgga gacaaaggtg      60
agatcaaata tatggaacaa ttgagtgaat attcgatgta tgaagattca gtgagtttgg     120
tgatcaaagg ccatgatatt gagctagaaa                                      150

<210> SEQ ID NO 48
<211> LENGTH: 150
<212> TYPE: DNA
<213> ORGANISM: Solanum lycopersicum

<400> SEQUENCE: 48
ctgcaagact ttttgagaac ttcagtgcga tgattaaatt agatgacgga gacaaaggtg      60
agatcaaata tatggaacaa ttgagtgaat attcgatgta tgaagattca gtgagtttgg     120
tgatcaaagg ccatgatatt gagctagaaa                                      150

<210> SEQ ID NO 49
<211> LENGTH: 150
<212> TYPE: DNA
<213> ORGANISM: Solanum lycopersicum

<400> SEQUENCE: 49
ctattccaat aaggatattt gttagcaata acatgaatat aatcttcaac aattctttga      60
attttatctc tagaaaaact tgtgatattt ggcaagtaaa tatattgaac aatatatgca     120
atactaattg gtataaaaaa gacatgagct                                      150

<210> SEQ ID NO 50
<211> LENGTH: 150
<212> TYPE: DNA
<213> ORGANISM: Solanum lycopersicum

<400> SEQUENCE: 50
ctattccaat aaggatattt gttagcaata acatgaatat aatcttcaac aattctttga      60
attttatctc tagaaaaact tgtgatattt ggcaagtaaa tatattgaac aatatatgca     120
atactaattg gtataaaaaa gacatgagct                                      150

<210> SEQ ID NO 51
<211> LENGTH: 150
<212> TYPE: DNA
<213> ORGANISM: Solanum lycopersicum

<400> SEQUENCE: 51
ctatggccca aattcactcc aaccatcact aattcaaagc ccaatataag tcagataatc      60
```

```
gaagaaagtt aagttccact caaatatgat atggatatgt ttggttattt tggcacagga    120
atacatagtt cgagcccaaa gtaatgagtt                                     150
```

<210> SEQ ID NO 52
<211> LENGTH: 150
<212> TYPE: DNA
<213> ORGANISM: Solanum lycopersicum

<400> SEQUENCE: 52

```
ctatggccca aattcactcc aaccatcact aattcaaagc ccaatataag tcagataatc    60
gaagaaagtt aagttccact caaatatgat atgtatatgt ttagttttt tggcacatga    120 atacatagtt caagcccaaa gtaatgagtt                                     150
```

<210> SEQ ID NO 53
<211> LENGTH: 150
<212> TYPE: DNA
<213> ORGANISM: Solanum lycopersicum

<400> SEQUENCE: 53

```
tttataacta tcttaatttt taaacttcat attaccactc catataataa tttaatattc    60
aacattttgt tttcaaatta tgctctaatt tttttttact actataatat atagtagtgt   120
atatgttttt tcaggatctc ataatcaatc                                     150
```

<210> SEQ ID NO 54
<211> LENGTH: 152
<212> TYPE: DNA
<213> ORGANISM: Solanum lycopersicum

<400> SEQUENCE: 54

```
tttataacta tcttaatttt taaacttcat attaccactc catataatat tttaatattc    60
aacattttga tttcaaatta tgctctaatt gttttttya ctactataat atatagtagt    120
gtatatgttt tttcaggatc tcataatcaa tc                                  152
```

<210> SEQ ID NO 55
<211> LENGTH: 150
<212> TYPE: DNA
<213> ORGANISM: Solanum lycopersicum

<400> SEQUENCE: 55

```
tttaatattc aacattttgt tttcaaatta tgctctaatt tttttttact actataaatat   60 atagtagtgt atatgttttt tcaggatctc ataatcaatc ttgtgattat tttggccatt   120
tttgcaaaga gggtaaaaat ggaagatcat                                    150
```

<210> SEQ ID NO 56
<211> LENGTH: 152
<212> TYPE: DNA
<213> ORGANISM: Solanum lycopersicum

<400> SEQUENCE: 56

```
tttaatattc aacattttga tttcaaatta tgctctaatt gtttttttya ctactataat    60
atatagtagt gtatatgttt tttcaggatc tcataatcaa tcttgtgatt attttggcca   120
tttttgcaaa gagggtaaaa atggaagatc at                                 152
```

<210> SEQ ID NO 57
<211> LENGTH: 150
<212> TYPE: DNA

<213> ORGANISM: Solanum lycopersicum

<400> SEQUENCE: 57

```
atgatgaatt ccttgattct atactcataa tagttgtcgt ttggatcctt caaaaattcc    60
tccaagttta tgtgtcggat ccttcaaaac gtatcatttt tgcagaatcc aagcaacata   120
gcttaactat gtattatttt ttgccaatag                                    150
```

<210> SEQ ID NO 58
<211> LENGTH: 150
<212> TYPE: DNA
<213> ORGANISM: Solanum lycopersicum

<400> SEQUENCE: 58

```
atgatgaatt ccttgattct atactcataa tagttgtcgt tcggatcctt taaaaattcc    60
tccaagttta tgtgtcggat ccttcaaacc gtatcatttt tgcagaatcc aaacaacata   120
gcttaactat gtattatttt ttgccaatag                                    150
```

<210> SEQ ID NO 59
<211> LENGTH: 150
<212> TYPE: DNA
<213> ORGANISM: Solanum lycopersicum

<400> SEQUENCE: 59

```
tcgaatgtca aaagttacat gttccataca ggatcgactt ttagcagata ttcatccatc    60
aaacaaacga ttcctgactt agttgatgat gacgatgatc acgtcaagtt tatcaaggaa   120
atgcaggatg agtttccatt actggaggca                                    150
```

<210> SEQ ID NO 60
<211> LENGTH: 150
<212> TYPE: DNA
<213> ORGANISM: Solanum lycopersicum

<400> SEQUENCE: 60

```
tcgaatgtca aaagttacat gttccataca ggatcgactt ttagcagata ttcatccatc    60
aaacaaacga ttcctgactt agttgatgat gacgatgatc acgtcaagtt tatcaaggaa   120
atgcaggatg agtttccatt actggaggca                                    150
```

<210> SEQ ID NO 61
<211> LENGTH: 150
<212> TYPE: DNA
<213> ORGANISM: Solanum lycopersicum

<400> SEQUENCE: 61

```
gacaaatccc tgctgcatat aatgattggt ttaaaaaaga caagaaaata cttgggattt    60
ttattttttt ttgagaaggt tgggttttat tattttagca ttggttattc ctcttaaggc   120
cttccacttc tccaactgcc aaataattga                                    150
```

<210> SEQ ID NO 62
<211> LENGTH: 150
<212> TYPE: DNA
<213> ORGANISM: Solanum lycopersicum

<400> SEQUENCE: 62

```
gacaaatccc tgctgcatat aatgattggt ttaaaaaaga caagaaaata cttgggattt    60
ttattttttt ttgagaaggt tgggttttat tattttagca ttggttattc ctcttaaggc   120
cttccacttc tccaactgcc aaataattga                                    150
```

<210> SEQ ID NO 63
<211> LENGTH: 150
<212> TYPE: DNA
<213> ORGANISM: Solanum lycopersicum

<400> SEQUENCE: 63

```
atttacttaa gagaagtatg caaattattt aaaagggaaa atcaatcaac ctttattgat      60
tgttacttta aaatatatgc aaaatcaacc tttaaaagat aaaatcaacc aacctttatt     120
aattaggaat aatttaataa attatatata                                      150
```

<210> SEQ ID NO 64
<211> LENGTH: 150
<212> TYPE: DNA
<213> ORGANISM: Solanum lycopersicum

<400> SEQUENCE: 64

```
atttacttaa aagaagtacg cggattattt aaaagggaaa atcaatcaac ctttattgat      60
tgttacttta aaatatatgc aaaatcaacc ttttaaagag aaaatcaacc aacctttatt     120
aattaggaat aatttaataa attatatata                                      150
```

<210> SEQ ID NO 65
<211> LENGTH: 150
<212> TYPE: DNA
<213> ORGANISM: Solanum lycopersicum

<400> SEQUENCE: 65

```
ataaacacac ataaaaatat aattttgatc ttatatatat accgtgtaat ttctaccaaa      60
tccctagctc cgcccttgag tcccgatact tccaacatta agaaataaat gagactctag     120
ttttagacat taataactac tcccattaac                                      150
```

<210> SEQ ID NO 66
<211> LENGTH: 150
<212> TYPE: DNA
<213> ORGANISM: Solanum lycopersicum

<400> SEQUENCE: 66

```
ataaacacac ataaaaatat aattttgatc ttatatatat accgtgcaat ttctaccaaa      60
tccctagctc cgcccatgag tcccgatact tccaacatta aaaataaat gagactctag      120 ttttagacat taataactac tcccattaac                                      150
```

<210> SEQ ID NO 67
<211> LENGTH: 150
<212> TYPE: DNA
<213> ORGANISM: Solanum lycopersicum

<400> SEQUENCE: 67

```
ttaatatttc ctgatgataa ctttctaact acggaattaa tctatgccac aggtgcaacc      60
tcgttcctgt ttacggaata ccagtatgtt ggtgttttca tggttgcttt tgcattactg     120
atctttctat tcctcggttc tgttgagggt                                      150
```

<210> SEQ ID NO 68
<211> LENGTH: 150
<212> TYPE: DNA
<213> ORGANISM: Solanum lycopersicum

<400> SEQUENCE: 68

```
ttaatatttc ctgatgataa ctttctaact acggaattaa tctatgccac aggtgcaacc    60
tcgttcctgt ttacggaata ccagtatgtt ggtgttttca tggttgcttt tgcattactg   120
atctttctat tcctcggttc tgttgagggt                                    150

<210> SEQ ID NO 69
<211> LENGTH: 150
<212> TYPE: DNA
<213> ORGANISM: Solanum lycopersicum

<400> SEQUENCE: 69
gacaaatccc tgctgcatat aatgattggt ttaaaaaaga caagaaaata cttgggattt    60
ttattttttt ttgagaaggt tgggttttat tattttagca ttggttattc ctcttaaggc   120
cttccacttc tccaactgcc aaataattga                                    150

<210> SEQ ID NO 70
<211> LENGTH: 150
<212> TYPE: DNA
<213> ORGANISM: Solanum lycopersicum

<400> SEQUENCE: 70
gacaaatccc tgctgcatat aatgattggt ttaaaaaaga caagaaaata cttgggattt    60
ttattttttt ttgagaaggt tgggttttat tattttagca ttggttattc ctcttaaggc   120
cttccacttc tccaactgcc aaataattga                                    150

<210> SEQ ID NO 71
<211> LENGTH: 150
<212> TYPE: DNA
<213> ORGANISM: Solanum lycopersicum

<400> SEQUENCE: 71
agaagtatgc aaattattta aagggaaaa tcaatcaacc tttattgatt gttactttaa     60
aatatatgca aaatcaacct ttaaaagata aaatcaacca acctttatta attaggaata   120
atttaataaa ttatatatat cttttataaa                                    150

<210> SEQ ID NO 72
<211> LENGTH: 150
<212> TYPE: DNA
<213> ORGANISM: Solanum lycopersicum

<400> SEQUENCE: 72
agaagtacgc ggattattta aagggaaaa tcaatcaacc tttattgatt gttactttaa     60
aatatatgca aaatcaacct tttaaagaga aaatcaacca acctttatta attaggaata   120
atttaataaa ttatatatat cttttataaa                                    150

<210> SEQ ID NO 73
<211> LENGTH: 150
<212> TYPE: DNA
<213> ORGANISM: Solanum lycopersicum

<400> SEQUENCE: 73
catacacatt gaagtgatcg atgaccgatg cataataaca atgttgaatt aatacctcct    60
caacaccttg gttacaggca tatatcaaag catcagcaag tgtgagccta ccctcagcat   120
cagtattgtt aacctcaatt gtcttaccat                                    150

<210> SEQ ID NO 74
<211> LENGTH: 150
```

```
<212> TYPE: DNA
<213> ORGANISM: Solanum lycopersicum

<400> SEQUENCE: 74
catacacatt gaagtgatcg atgaccgatg cataataaca acgttgaatt aataccttct      60
caacaccttg gttacaggca tatatcaaag catcagcaag tgtgagccta ccctcagcat     120
cagtattgtt aacctcaatt gtcttaccat                                      150

<210> SEQ ID NO 75
<211> LENGTH: 150
<212> TYPE: DNA
<213> ORGANISM: Solanum lycopersicum

<400> SEQUENCE: 75
catatgtaag atggcaatat taggcatttt ataaatcaat atctaagtct actagtgcct      60
tttcttttcc accattttca ccccaaattt attcataaaa acttgatgca aattcttttc     120
tcaaacatcc ataagtccct tgagattaca                                      150

<210> SEQ ID NO 76
<211> LENGTH: 150
<212> TYPE: DNA
<213> ORGANISM: Solanum lycopersicum

<400> SEQUENCE: 76
catatgtaag atggcaatat taggcatttt ataaatcaat atctaagtct actagtgcct      60
tttcttttcc accattttca ccccaaattt attcataaaa acttgatgca aattcttttc     120
tcaaacatcc ataagtccct tgagattaca                                      150

<210> SEQ ID NO 77
<211> LENGTH: 150
<212> TYPE: DNA
<213> ORGANISM: Solanum lycopersicum

<400> SEQUENCE: 77
gtttgtataa aaatatttta cattatcgat gcatataaga taaaatgata gggttttcat      60
ttagaccact agattttctt gagcatatga caaaaataca cattaaatag aatttgtctt     120
gtgttatgtg tttccatatg gtaagaattt                                      150

<210> SEQ ID NO 78
<211> LENGTH: 150
<212> TYPE: DNA
<213> ORGANISM: Solanum lycopersicum

<400> SEQUENCE: 78
gtttgtataa aaatatttta cattatcaat gcatataaga taaaatgata gggttttcat      60
ttagaccact agattttctt gagcatatga caaaaataca aattaaatag aatttgtctt     120
gtgttatgtg tttccatatg gtaagaattt                                      150

<210> SEQ ID NO 79
<211> LENGTH: 150
<212> TYPE: DNA
<213> ORGANISM: Solanum lycopersicum

<400> SEQUENCE: 79
atgcatataa gataaaatga tagggttttc atttagacca ctagattttc ttgagcatat      60
gacaaaaata cacattaaat agaatttgtc ttgtgttatg tgtttccata tggtaagaat     120
```
tttgtggagg cttttgcaga tgcagtaaaa                                150

<210> SEQ ID NO 80
<211> LENGTH: 150
<212> TYPE: DNA
<213> ORGANISM: Solanum lycopersicum

<400> SEQUENCE: 80
atgcatataa gataaaatga tagggttttc atttagacca ctagattttc ttgagcatat    60
gacaaaaata caaattaaat agaatttgtc ttgtgttatg tgtttccata tggtaagaat   120
tttgtggagg cttttgtaga tgcagtaaaa                                   150

<210> SEQ ID NO 81
<211> LENGTH: 150
<212> TYPE: DNA
<213> ORGANISM: Solanum lycopersicum

<400> SEQUENCE: 81
tagtgtgtac gcaaaacctt aaccctacct cagaaggcag agaagaggct gtttccaata    60
acactaaacc taatgcagca cagtaaattt cccaacttta actactctac aagcaagaat   120
cgatgaaaat tgacacaaaa actgttcaaa                                   150

<210> SEQ ID NO 82
<211> LENGTH: 150
<212> TYPE: DNA
<213> ORGANISM: Solanum lycopersicum

<400> SEQUENCE: 82
tagtgtgtac gcaaaacctt aaccctacct cagaaggcag agaagaggct gtttccaata    60
acactaaacc taatgcagca cagtaaattt cccaacttta acaactctac aagcaagaat   120
cgatgaaatt tgacacaaaa actgttcaaa                                   150

<210> SEQ ID NO 83
<211> LENGTH: 150
<212> TYPE: DNA
<213> ORGANISM: Solanum lycopersicum

<400> SEQUENCE: 83
cagaaggcag agaagaggct gtttccaata acactaaacc taatgcagca cagtaaattt    60
cccaacttta actactctac aagcaagaat cgatgaaaat tgacacaaaa actgttcaaa   120
caactacata agcagaaaac agagcaagaa                                   150

<210> SEQ ID NO 84
<211> LENGTH: 150
<212> TYPE: DNA
<213> ORGANISM: Solanum lycopersicum

<400> SEQUENCE: 84
cagaaggcag agaagaggct gtttccaata acactaaacc taatgcagca cagtaaattt    60
cccaacttta acaactctac aagcaagaat cgatgaaatt tgacacaaaa actgttcaaa   120
caactacata agcagaaaac agagcaagaa                                   150

<210> SEQ ID NO 85
<211> LENGTH: 150
<212> TYPE: DNA
<213> ORGANISM: Solanum lycopersicum

<400> SEQUENCE: 85

```
tttaatatgg tgtgataata tattgtcatc gatcaatcat gtcaaatgca gtttgatcga      60
tcttttttga ctcgtaagta attattttc ctatggagag agggacttca agttcttaca      120
aagagttagt gtaaaatagt ttatgtatga                                      150

<210> SEQ ID NO 86
<211> LENGTH: 150
<212> TYPE: DNA
<213> ORGANISM: Solanum lycopersicum

<400> SEQUENCE: 86
tttaatatgg tgtgataata tattgtcatc gatcaatcat gtcaaatgca gtttgatcga      60
tcttttttga ctcgtaagta attattttc ctatggagag agggacttca agttcttaca      120
aagagttagt gtaaaatagt ttatgtatga                                      150

<210> SEQ ID NO 87
<211> LENGTH: 150
<212> TYPE: DNA
<213> ORGANISM: Solanum lycopersicum

<400> SEQUENCE: 87
agaaaaaaaa aacaaattac attaaacagt aagcattaaa acaacaatct caacaatgtt      60
tttttttttt tttagtcaaa tttgcactaa attctttgta cttactaaca agattttgtt      120
aacccaagaa aaaagtttga gtaaaaaaaa                                      150

<210> SEQ ID NO 88
<211> LENGTH: 149
<212> TYPE: DNA
<213> ORGANISM: Solanum lycopersicum

<400> SEQUENCE: 88
agaaaaaaaa caaaattaca ttaaacagta agcattaaaa caacaatctc aacaatgttt      60
tttttttttt ttwktywwwt ttkcactaaa ttctttgtac ttactaacaa gattttgttt      120
acccaagaaa aaagcttgag ttaagaaaa                                       149

<210> SEQ ID NO 89
<211> LENGTH: 150
<212> TYPE: DNA
<213> ORGANISM: Solanum lycopersicum

<400> SEQUENCE: 89
tttatagttt gtttcaaaaa gaacgtctct tttttaaatt cttttggcaa ttctatactt      60
ctaactttca cctaacatat ttaagtataa attttggagg attcgatgta gaagcatttt      120
tgtagagact gagcaacata ggtctgcccg                                      150

<210> SEQ ID NO 90
<211> LENGTH: 150
<212> TYPE: DNA
<213> ORGANISM: Solanum lycopersicum

<400> SEQUENCE: 90
tttatagttt gtttcaaaaa gaacgtcgct tttttaaatt cttttggcaa ttctataatt      60
ctaactttca cctaacatat ttaagtataa attttggagg attcgatgta gaagcatttt      120
tgtagagact gagcaacata ggtctgcccg                                      150

<210> SEQ ID NO 91
```

<211> LENGTH: 150
<212> TYPE: DNA
<213> ORGANISM: Solanum lycopersicum

<400> SEQUENCE: 91

```
tagcttttgc ctagtccccg acactcctat atgtaccaac ctcaaccagc ccgagctggt    60
caccaaccca accgtttctc ctccaaattc aattttttt tctctctcac actcactata    120
cttcactctc tttctctctc caaaactcca                                     150
```

<210> SEQ ID NO 92
<211> LENGTH: 151
<212> TYPE: DNA
<213> ORGANISM: Solanum lycopersicum
<220> FEATURE:
<221> NAME/KEY: misc_feature
<222> LOCATION: (150)..(150)
<223> OTHER INFORMATION: This nucleotide may be absent

<400> SEQUENCE: 92

```
tagcttttgc ctagtccccg acactcctat atgtaccaac ctcaaccagc ccgagctggt    60
caccaaccca accgtttctc ctccaaattc aattttttt tctctctcac actcactata    120
cttcactctc tttctctctc caaaactcca a                                   151
```

<210> SEQ ID NO 93
<211> LENGTH: 150
<212> TYPE: DNA
<213> ORGANISM: Solanum lycopersicum

<400> SEQUENCE: 93

```
ccatatttat ctttgtcaag aacattgttc cccaatactg tttgagaaaa aaataagcac    60
gaagatggat tcttttaca tgacgtacat ggaaaaatac atatttggat tcctcttgag    120
aattaatagt tgaagttagc tatctgattt                                     150
```

<210> SEQ ID NO 94
<211> LENGTH: 150
<212> TYPE: DNA
<213> ORGANISM: Solanum lycopersicum

<400> SEQUENCE: 94

```
ccatatttat ctttgtcaag aacattgttc cccaatactg tttgagaaaa aaataagcac    60
gaagatggat tcttttaca tgacgtacat ggaaaaatac atatttggat tcctcttgag    120
aattaatagt tgaagttagc tatctgattt                                     150
```

<210> SEQ ID NO 95
<211> LENGTH: 150
<212> TYPE: DNA
<213> ORGANISM: Solanum lycopersicum

<400> SEQUENCE: 95

```
ggctttcagc catgctgttg ctgcttgcct ttctgactgg agtatggaag gtaagttgtt    60
ttctgtcact attaatcaac cgttgggtga tgcttctgtt gataatctta gagctttact    120
atctgtgaag aaccctcttg tgctcaacgg                                     150
```

<210> SEQ ID NO 96
<211> LENGTH: 150
<212> TYPE: DNA
<213> ORGANISM: Solanum lycopersicum

<400> SEQUENCE: 96

```
ggctttcagc catgctgttg ccgcttgcct ttctgactgg agtatggaag gtaagttgtt    60
ttctgtcact attaatcaac cgttgggtga tgctgctgtt gataatctta gagctttact   120
atctgtgaag aatcctcttg tgctcaacgg                                    150
```

<210> SEQ ID NO 97
<211> LENGTH: 150
<212> TYPE: DNA
<213> ORGANISM: Solanum lycopersicum

<400> SEQUENCE: 97

```
aagtcgaaca agttccatgg acatttaagt agtaggaaga agttttactt tcccaagttg    60 cggattttg atctctcttg taacaaattt agcggctcac tacctgcaag acttttgag    120 aacttcagtg cgatgattaa attagatgac                                    150
```

<210> SEQ ID NO 98
<211> LENGTH: 150
<212> TYPE: DNA
<213> ORGANISM: Solanum lycopersicum

<400> SEQUENCE: 98

```
aagtcgaaca agttccatgg acatttaagt agtaggaaga agttttactt tcccaagttg    60 cggattttg atctctcttg taacaaattt agcggctcac tacctgcaag acttttgag    120 aacttcagtg cgatgattaa attagatgac                                    150
```

<210> SEQ ID NO 99
<211> LENGTH: 150
<212> TYPE: DNA
<213> ORGANISM: Solanum lycopersicum

<400> SEQUENCE: 99

```
aatcaacact attatgacaa cgatagatct ctcaagcaac cattttgaag gtgtcattcc    60
gaaatcacta aaggatctca gctcacttcg gttactcaat ttatcccgta acaatctcaa   120
aggtgatatt ccaatcgaat tgggacaatt                                    150
```

<210> SEQ ID NO 100
<211> LENGTH: 150
<212> TYPE: DNA
<213> ORGANISM: Solanum lycopersicum

<400> SEQUENCE: 100

```
aatcaacact attatgacaa cgatagatct ctcaagcaac cattttgaag gtgtcattcc    60
gaaatcacta aaggatctca gctcacttcg gttactcaat ttatcccgta acaatctcaa   120
aggtgatatt ccaatcgaat tgggacaatt                                    150
```

<210> SEQ ID NO 101
<211> LENGTH: 150
<212> TYPE: DNA
<213> ORGANISM: Solanum lycopersicum

<400> SEQUENCE: 101

```
cattaggatg tgaagctaaa aaatgtctat ttttactttc catttcacca atgaaatgac    60
cttcaattgc atatatattt ttcattggtc cattgtgtat cattggtata tctccttctt   120
tgtatgtcca cactttgaat ctctttaaca                                    150
```

<210> SEQ ID NO 102

```
<211> LENGTH: 150
<212> TYPE: DNA
<213> ORGANISM: Solanum lycopersicum

<400> SEQUENCE: 102
cattaggatg tgaagctaaa aaatgtctat ttttactttc catttcacca atgaaatgac      60
cttcaattgc atatatattt ttcattggtc cattgtgtat cattggtata tctccttctt     120
tgtatgtcca cactttgaat ctctttaaca                                      150

<210> SEQ ID NO 103
<211> LENGTH: 150
<212> TYPE: DNA
<213> ORGANISM: Solanum lycopersicum

<400> SEQUENCE: 103
gattgatcac catagaactt gctctaaatc cgtctcagac tatacgtaac tcctcgtaaa      60
taacaagtta ttgttcctat atgtatcaaa catatatcac accattatcc ctcttctatc     120
tattatgaca tccgaatcga gtcctgtatt                                      150

<210> SEQ ID NO 104
<211> LENGTH: 150
<212> TYPE: DNA
<213> ORGANISM: Solanum lycopersicum

<400> SEQUENCE: 104
gattgatcac catagaactt gctctaaatc cgtctcagac tatacataac tcttcgtaaa      60
taacaagtta ttgttcctat atgtatcaaa catatatcac atcattatcc ctcttctatc     120
tattatgaca tccgaatcga gtcctgtatt                                      150

<210> SEQ ID NO 105
<211> LENGTH: 17
<212> TYPE: DNA
<213> ORGANISM: Solanum lycopersicum

<400> SEQUENCE: 105
ccaatgatcg ataaagc                                                     17

<210> SEQ ID NO 106
<211> LENGTH: 20
<212> TYPE: DNA
<213> ORGANISM: Solanum lycopersicum

<400> SEQUENCE: 106
tgattcacca actcatatag                                                  20

<210> SEQ ID NO 107
<211> LENGTH: 16
<212> TYPE: DNA
<213> ORGANISM: Solanum lycopersicum

<400> SEQUENCE: 107
actgcagacg ttctta                                                      16

<210> SEQ ID NO 108
<211> LENGTH: 19
<212> TYPE: DNA
<213> ORGANISM: Solanum lycopersicum

<400> SEQUENCE: 108
caattattgt tgtaaattt                                                   19
```

```
<210> SEQ ID NO 109
<211> LENGTH: 16
<212> TYPE: DNA
<213> ORGANISM: Solanum lycopersicum

<400> SEQUENCE: 109
caaccaatga taaagc                                                      16

<210> SEQ ID NO 110
<211> LENGTH: 18
<212> TYPE: DNA
<213> ORGANISM: Solanum lycopersicum

<400> SEQUENCE: 110
attcaccaac taatatag                                                    18

<210> SEQ ID NO 111
<211> LENGTH: 15
<212> TYPE: DNA
<213> ORGANISM: Solanum lycopersicum

<400> SEQUENCE: 111
ctgcagacat tctta                                                       15

<210> SEQ ID NO 112
<211> LENGTH: 18
<212> TYPE: DNA
<213> ORGANISM: Solanum lycopersicum

<400> SEQUENCE: 112
caattattgt tgaaattt                                                    18

<210> SEQ ID NO 113
<211> LENGTH: 28
<212> TYPE: DNA
<213> ORGANISM: Solanum lycopersicum

<400> SEQUENCE: 113
gtgtttaata actaagcacc cttcgttt                                         28

<210> SEQ ID NO 114
<211> LENGTH: 25
<212> TYPE: DNA
<213> ORGANISM: Solanum lycopersicum

<400> SEQUENCE: 114
gggaaggatg tagaaactgg acttt                                            25

<210> SEQ ID NO 115
<211> LENGTH: 30
<212> TYPE: DNA
<213> ORGANISM: Solanum lycopersicum

<400> SEQUENCE: 115
ttgtgtggct ataaaatcat ctcaatgaga                                       30

<210> SEQ ID NO 116
<211> LENGTH: 25
<212> TYPE: DNA
<213> ORGANISM: Solanum lycopersicum

<400> SEQUENCE: 116
```

```
ttgcttctga tattacaccg tccaa                                          25

<210> SEQ ID NO 117
<211> LENGTH: 25
<212> TYPE: DNA
<213> ORGANISM: Solanum lycopersicum

<400> SEQUENCE: 117
tggctacact tgttccatct aggta                                          25

<210> SEQ ID NO 118
<211> LENGTH: 34
<212> TYPE: DNA
<213> ORGANISM: Solanum lycopersicum

<400> SEQUENCE: 118
gtaagcaggt cattcttaac ttatactaat aaat                                34

<210> SEQ ID NO 119
<211> LENGTH: 25
<212> TYPE: DNA
<213> ORGANISM: Solanum lycopersicum

<400> SEQUENCE: 119
tctccattta tgtggcacaa ttcca                                          25

<210> SEQ ID NO 120
<211> LENGTH: 24
<212> TYPE: DNA
<213> ORGANISM: Solanum lycopersicum

<400> SEQUENCE: 120
agctaacagg ctgcaattaa cctt                                           24
```